US008537333B2

(12) United States Patent
Freimann et al.

(10) Patent No.: US 8,537,333 B2
(45) Date of Patent: Sep. 17, 2013

(54) OPTICAL IMAGING DEVICE WITH IMAGE DEFECT DETERMINATION

(75) Inventors: Rolf Freimann, Aalen (DE); Ulrich Wegmann, Koenigsbronn (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 440 days.

(21) Appl. No.: 12/983,735

(22) Filed: Jan. 3, 2011

(65) Prior Publication Data

US 2011/0164232 A1    Jul. 7, 2011

Related U.S. Application Data

(63) Continuation of application No. PCT/EP2009/058224, filed on Jun. 30, 2009.

(60) Provisional application No. 61/133,616, filed on Jul. 1, 2008.

(30) Foreign Application Priority Data

Jul. 1, 2008    (DE) .......................... 10 2008 030 664

(51) Int. Cl.
*G03B 27/42*    (2006.01)

(52) U.S. Cl.
USPC ................... 355/53; 355/30; 355/55; 355/63; 355/67; 355/77

(58) Field of Classification Search
USPC ............. 355/30, 53, 55, 63, 67, 77; 356/352, 356/357, 399, 400, 496, 512, 521
See application file for complete search history.

(56) References Cited

U.S. PATENT DOCUMENTS 4,537,473 A    8/1985  Maschmeyer
5,555,089 A    9/1996  Dunn et al.

(Continued)

FOREIGN PATENT DOCUMENTS

DE    10 2005 056 914 A1    5/2007

(Continued)

OTHER PUBLICATIONS

Brinkmann, S., "A Method for Testing Rod-Shaped Technical Objects by Means of Computer-Generated Holograms and Grazing Incidence Interferometry", Dissertation, Hamburg, Scientific Faculties of Friedrich-Alexander University at Erlangen-Nuernberg, Jun. 23, 1999.

(Continued)

*Primary Examiner* — Steven H Whitesell Gordon
*Assistant Examiner* — Mesfin T Asfaw
(74) *Attorney, Agent, or Firm* — Sughrue Mion, PLLC

(57)    ABSTRACT

An optical imaging device, in particular for microlithography, including an imaging unit adapted to image an object point on an image point and a measurement device. The imaging unit has a first optical element group having at least one first optical element. The imaging device is adapted to participate in the imaging of the object point on the image point, and the measurement unit is adapted to determine at least one image defect occurring on the image point when the object point is imaged. The measuring device includes at least one measurement light source, one second optical element group and at least one detection unit. The measurement light source transmits at least one measurement light bundle. The second optical element group includes at least one optical reference element and one second optical element, the elements adapted to direct the at least one measurement light bundle to the at least one detection unit, to produce at least one detection signal. The second optical element has a defined spatial relationship with the first optical element. The optical reference element has an at least partially reflecting first optical surface and the second optical element has an at least partially reflecting second optical surface. The measurement device is adapted to determine the at least one image defect using the at least one detection signal. The first optical surface and the second optical surface are positioned relative to one another such that a multiple reflection of the at least one measurement light bundle occurs between them.

23 Claims, 7 Drawing Sheets

(56) References Cited

U.S. PATENT DOCUMENTS

| | | |
|---|---|---|
| 7,221,460 B2 | 5/2007 | Ohtsuka |
| 7,226,177 B2 | 6/2007 | Sasaki et al. |
| 2003/0234993 A1 | 12/2003 | Hazelton et al. |
| 2004/0227915 A1 | 11/2004 | Ohtsuka |
| 2009/0002663 A1 | 1/2009 | Freimann et al. |

FOREIGN PATENT DOCUMENTS

| | | | |
|---|---|---|---|
| JP | 6153602 A | 3/1986 | |
| JP | 2004-246060 A | 9/2004 | |
| JP | 2004266264 A | 9/2004 | |
| JP | 2004343078 A | 12/2004 | |
| JP | 2005303206 A | 10/2005 | |
| JP | 2008543070 A | 11/2008 | |
| WO | 2006/102997 A1 | 10/2006 | |

OTHER PUBLICATIONS

P. Hariharan, "Optical Shop Testing, Third Edition", 2007, John Wiley & Sons, pp. 259-274.

OPTICAL IMAGING DEVICE WITH IMAGE DEFECT DETERMINATION

CROSS-REFERENCE TO RELATED APPLICATIONS

This is a Continuation of International Application PCT/EP2009/058224, with an international filing date of Jun. 30, 2009, which was published under PCT Article 21(2) in German, and the complete disclosure of which, including amendments, is incorporated into the present application by reference. The present application claims the priority of German Patent Application 10 2008 030 664.9 and of U.S. Provisional Patent Application 61/133,616, both filed on Jul. 1, 2008, and the contents of both of which are also incorporated into the present application by reference.

FIELD OF AND BACKGROUND OF THE INVENTION

The present invention relates to optical imaging devices. The invention can be used in connection with microlithography, e.g. as employed for the production of microelectronic circuits. It therefore furthermore relates to an imaging method.

Particularly in the field of microlithography, besides using components made with the greatest possible precision, it is necessary inter alia to position the components of the imaging device, for example the optical elements such as lenses or mirrors, as exactly as possible in order to achieve a correspondingly high image quality. The high accuracy requirements, which are in the microscopic range of the order of a few nanometers or less, are not least a consequence of the constant need to increase the resolution of the optical systems used for the production of microelectronic circuits, in order to push forward miniaturisation of the microelectronic circuits to be produced.

With increased resolution, and the generally concomitant reduction of the wavelength of the light being used, not only do the requirements for the positioning accuracy of the optical elements used increase. Also, the requirements with respect to minimising the imaging errors of the overall optical arrangement increase.

In order to comply with the stringent requirements for positioning the components involved with the short wavelengths in the ultraviolet (UV) range used in microlithography, for example with wavelengths in the region of 193 nm, but also particularly in the so-called extreme UV range (EUV) with working wavelengths in the range of from 5 nm to 20 nm (usually in the region of 13 nm), it is often proposed to capture the positions of the individual components such as the mask stage, the optical elements and the substrate stage (for example a wafer stage), respectively and individually with respect to a reference (for example a reference structure, which is often formed by a so-called metrology frame) and then to position these components actively with respect to one another. Such a procedure is known for example from U.S. Pat. No. 7,221,460 B2 (Ohtsuka), the entire disclosure of which is incorporated herein by reference.

This solution has on the one hand the disadvantage that, generally, no real time measurement of the position of the image of the projection pattern of the mask on the substrate (usually a wafer) is carried out, but instead the relative position of the components and the position of the image are merely deduced indirectly from the individual position data of the components. In this case, the respective measurement errors add up, so that a comparatively high overall measurement error can sometimes occur. Furthermore, this entails a large number of elements to be positioned accurately, all of which have to be positioned and measured with respect to their position with the corresponding angular accuracy in the nanorad range (nrad) or less and a translation accuracy in the picometer range (pm). This also leads to particularly stringent requirements for the thermal stability of the reference and the support structure for the optical elements. Here, only a few dozens of nanometers per kelvin (nm/K) are generally permissible in respect of the thermal expansion.

On the other hand, a range of solutions is also known in which the quality of the imaging of the object points of an object plane (projection pattern of the mask) onto the image points in an image plane (in which the substrate is to be arranged), particularly the position of the image of the projection pattern in the image plane, is determined in real time. In this case, the imaging quality, particularly the position of the image of the projection pattern on the image plane, can in principle be corrected with far fewer active elements, and sometimes even with just one active element. Not only does this simplify the dynamic driving of the other components, but also much less stringent requirements need to be placed on the thermal stability of the reference and the support structure for the optical elements.

For example, it is known to determine the aberrations of the projection beam path directly, i.e. with wavefront sensors arranged in the image plane at the position of the substrate. To this end, however, the exposure operation of the substrate needs to be interrupted. This is a practicable solution for projection devices which are sufficiently stable as a function of time, that is to say the monitoring and correction of imaging errors can be carried out at sufficiently large time intervals (from a few hours to days or even weeks). Measurement and correction at shorter time intervals, as would be necessary for perturbations acting within a short time (for example thermal perturbations), is either not possible since the measurement would in principle take too long, or is undesirable since the exposure process ought not to be interrupted or the effects on the productivity of the imaging device are unacceptable.

Real time determination of the position of the image of the projection pattern of the mask on the substrate is often carried out according to the so-called laser pointing principle. In this case, a measurement light bundle in the form of a collimated light beam is guided from a light source arranged in the region of the mask in the vicinity of the path of the useful light (i.e. at the image field edge) via the optical elements involved in the imaging as far as into the region of the substrate, and captured there by a detector. Even very small deviations of the optical elements from their setpoint positions then generate a deviation of the light beam from its setpoint position, which is captured by the detector and used for correction. Such a method is known for example from US 2003/0234993 A1 (Hazelton et al.), the entire disclosure of which is also incorporated herein by reference.

Here, owing to the guiding of the laser beam via the optical elements involved in the imaging, it is sometimes not only possible to determine deviations with respect to the correct position of the image of the projection pattern of the mask on the substrate, but moreover other errors (for example distortions etc.) in the imaging can be captured. All these position errors and other errors are combined under the term imaging error in the present description.

These variants for determination of the imaging error, however, often require intervention in the projection beam path (for example by introducing beam splitters) and sometimes entail an undesired loss of radiation power etc.

As already mentioned, the problems explained above in relation to the angular accuracy and the translation accuracy for the positioning and orientation of the components involved in the imaging have particularly great repercussions in imaging devices which operate in the EUV range (for example in the 13.5 nm wavelength range), as is known for example from U.S. Pat. No. 7,226,177 B2 (Sasaki et al.), the entire disclosure of which is also incorporated herein by reference.

These objectives currently operate exclusively with reflective optical elements (that is to say mirrors or the like), which guide the EUV light by reflection, with, mostly, four, six or eight mirrors mostly being used. During operation of the imaging device, these mirrors generally change their position and/or orientation (owing to mechanical and/or thermal perturbations), since the support structure cannot be absolutely stable (mechanically and/or thermally).

The beam path in such an EUV objective may be a plurality of meters long. In the systems known from U.S. Pat. No. 7,226,177 B2 (Sasaki et al.), for instance, the individual spacings of the optical surfaces lead to an overall beam path length of about 2.5 m from the first mirror (M1) to the plane of the substrate to be exposed. In relation to this, a permissible image displacement with structures to be exposed in the region of about 25 nm must also lie only in the nm range. An admissible image displacement of 1 nm in this case entails a maximum permissible mirror tilt of only 0.2 nrad for the first mirror M1. For the subsequent mirrors (M2 to M6) in the beam path, these angular tolerances increase stepwise since their distances from the plane of the substrate become smaller and smaller.

A correspondingly precise measurement (and subsequent correction) of the alignment of such mirrors, however, is not possible with the previously known devices. There are furthermore combinations of mirror tilts whose effects in relation to the overall image displacement cancel out, and therefore do not cause any image displacement. Such mirror tilt combinations nevertheless lead to deviations of the wavefront, that is to say aberrations, which cannot, however, be identified with the previous methods.

SUMMARY OF THE INVENTION

It is an object of the present invention to provide an optical imaging device and/or an imaging method which do not have the disadvantages mentioned above, or at least have them to a lesser extent, and particularly which straightforwardly allow maximally direct determination and, if appropriate, correction of imaging errors in real time.

It is furthermore an object of the invention to provide an optical imaging device and/or an imaging method which allow maximally direct determination and, if appropriate, correction of imaging errors with few elements.

It is furthermore an object of the invention to provide an optical imaging device and/or an imaging method which allow maximally precise determination and, if appropriate, correction of imaging errors due to a change in the orientation of the optical elements.

The present invention is based on the cognition that such a direct determination and if appropriate correction of imaging errors of an imaging unit is readily possible in real time in parallel with the actual imaging process (for example the exposure of a substrate or the like) if the determination of the imaging error is carried out by means of a separate measuring device having measurement light source, capturing unit and separate measurement optics, the optical elements of which guide a measurement light bundle from the measurement light source onto the capturing unit and are respectively in a relationship, defined at all times, with one of the optical elements of the imaging unit. The relationship, defined at all times, between the respective optical elements of the measurement optics and one of the optical elements of the imaging unit ensures that a state change (change in position and/or orientation) of one of the optical elements of the imaging unit leads to a defined change in the aberrations of the measurement optics and therefore in the capturing signal of the capturing unit, which can in turn be assigned to a corresponding imaging error of the imaging unit.

The optical elements of the measurement optics, which are at least in part arranged separately, make it possible to configure the measurement optics so that only (if at all) a small impairment of the imaging actually carried out by the imaging unit takes place owing to the measurement carried out in parallel with the actual imaging.

Unlike in the previously known solutions, the measurement optics can furthermore be configured advantageously so that the changes in the capturing signal can be assigned as unequivocally as possible to the individual state changes of the optical elements of the imaging unit. The sensitivity of the measurement optics in all degrees of freedom is known beforehand, for example having been calculated and/or determined experimentally (for example a change in the Z7/Z8 coma centring and the Z5/Z6 astigmatism centring corresponds to the ratio 4:1 for a translation of a lens etc.).

In the event of poor conditioning of individual measurement optical elements (for example low sensitivity, uniqueness, separability or orthogonality of the equation system of the individual sensitivities etc.) it is readily possible to improve the conditioning by adding extra measuring systems. This may, for example, be done by linking an extra measuring system of the same type to a different location on the imaging unit (for example rotated through 90° or 180° with respect to an optical axis of the imaging unit). Likewise, controlled optimisation or adaptation of the conditioning of two or more different measurement optical elements may be carried out. The measurement optics may (individually or in any desired combination) consist of refractive, diffractive and reflective optical elements of any configuration (spherical, aspherical, cylindrical, plane optical surfaces or freeform surfaces).

The present invention therefore relates to an optical imaging device, in particular for microlithography, having an imaging unit for imaging an object point on an image point and a measuring device, wherein the imaging unit comprises a first optical element group having at least one first optical element, which is adapted to participate in the imaging of the object point on the image point, and the measuring device is adapted to determine at least one imaging error which occurs when imaging the object point on the image point. The measuring device comprises at least one measurement light source, a second optical element group and at least one capturing unit, the measurement light source emitting at least one measurement light bundle. The second optical element group comprises a plurality of second optical elements, which are adapted to guide the at least one measurement light bundle onto the at least one capturing unit in order to generate at least one capturing signal. Each second optical element is in a defined spatial relationship with one of the first optical elements, at least one second optical element being different from the first optical elements. The measuring device is adapted to determine the at least one imaging error by using the at least one capturing signal.

The present invention also relates to an imaging method, in particular for microlithography, in which an object point is imaged on an image point by an imaging unit, the imaging unit comprising a first optical element group having a plurality of first optical elements which participate in the imaging of the object point on the image point, and a measuring device determining at least one imaging error which occurs when imaging the object point on the image point. The measuring device comprises at least one measurement light source, a second element group and at least one capturing unit, the measurement light source emitting at least one measurement light bundle. The at least one measurement light bundle is guided by means of a plurality of second optical elements of the second optical element group onto the at least one capturing unit in order to generate at least one capturing signal. Each second optical element is in a defined spatial relationship with the first optical element, at least one second optical element being different from the first optical elements. The measuring device determines the at least one imaging error by using the at least one capturing signal.

The present invention is furthermore based on the cognition that precise determination and if appropriate correction of imaging errors of an imaging unit caused by a change in the orientation (tilting) of optical elements of the imaging unit is readily possible in real time in parallel with the actual imaging process (for example the exposure of a substrate or the like) if the determination of the imaging error is carried out by means of a separate measuring device having measurement light source, capturing unit and measurement optics, the optical elements of which guide a measurement light bundle from the measurement light source onto the capturing unit. One of the optical elements of the measurement optics has at all times a defined relationship with one of the optical elements of the imaging unit, and is assigned to a reference element of the measurement optics so that multiple reflection of the measurement light bundle takes place between the reference element and the assigned element of the measurement optics.

The effect achieved by this direct multiple reflection of the measurement light bundle (and thus multiple passage through the optical cavity formed by the reference element and the optical element of the measurement optics) between these two optical elements is that an angular deviation or tilts between these two elements of the measurement optics is incorporated into the measurement wavefront while being multiplied by a factor depending on the number of reflections. Finally, the multiple reflection thus achieves optical amplification which results in an increase of the angular resolution of the measuring device. With a correspondingly large number of reflections in the optical cavity, it is readily possible to achieve angular resolutions in the sub-nrad range.

With a usual interferometric measurement, for example, reliable detection of wavefront angular tilts of $\lambda/1000$ over a predetermined measurement aperture is possible. If this measurement aperture has a diameter of 100 mm, for example, then this corresponds to an angular resolution of 6 nrad when the measurement wavelength $\lambda$ is the wavelength of a conventional helium-neon laser. As already explained in the introduction, however, the requirements for the angular resolution of the measuring device are at least a factor of 10 greater. Yet with the invention, this problem can be resolved simply by a correspondingly large number of reflections inside the optical cavity.

The relationship, defined at all times, between the optical element of the measurement optics and one of the optical elements of the imaging unit furthermore ensures that a state change (change in position and/or orientation) of one of the optical elements of the imaging unit leads to a defined change in the aberrations of the measurement optics and therefore in the capturing signal of the capturing unit, which can in turn be assigned to a corresponding imaging error of the imaging unit.

The present invention therefore also relates to an optical imaging device, in particular for microlithography, having an imaging unit for imaging an object point on an image point and a measuring device, wherein the imaging unit comprises a first optical element group having at least one first optical element, which is adapted to participate in the imaging of the object point on the image point, and the measuring device is adapted to determine at least one imaging error which occurs when imaging the object point on the image point. The measuring device comprises at least one measurement light source, a second optical element group and at least one capturing unit, the measurement light source emitting at least one measurement light bundle. The second optical element group comprises at least one optical reference element and one second optical element, which are adapted to guide the at least one measurement light bundle onto the at least one capturing unit in order to generate at least one capturing signal. The second optical element has a defined spatial relationship with the first optical element. The optical reference element has an at least partially reflective first optical surface, while the second optical element has an at least partially reflective second optical surface. The measuring device is adapted to determine the at least one imaging error by using the at least one capturing signal. The first optical surface and the second optical surface are assigned to one another so that multiple reflection of the at least one measurement light bundle takes place between them.

The present invention furthermore relates to an imaging method, in particular for microlithography, in which an object point is imaged on an image point by an imaging unit, a first optical element group of the imaging unit having at least one first optical element participating in the imaging of the object point on the image point, and a measuring device determining at least one imaging error which occurs when imaging the object point on the image point. The measuring device comprises at least one measurement light source, a second element group and at least one capturing unit, the measurement light source emitting at least one measurement light bundle. In order to generate at least one capturing signal, at least one optical reference element and a second optical element of the second optical element group guide the at least one measurement light bundle onto the at least one capturing unit, the second optical element having a defined spatial relationship with the first optical element. The optical reference element has an at least partially reflective first optical surface, while the second optical element has an at least partially reflective second optical surface. The measuring device determines the at least one imaging error by using the at least one capturing signal. The first optical surface and the second optical surface are assigned to one another so that multiple reflection of the at least one measurement light bundle takes place between them.

The present invention furthermore relates to an optical imaging device, in particular for microlithography, having an imaging unit for imaging an object point on an image point and a measuring device, the measuring device being adapted to determine at least one imaging error which occurs when imaging the object point on the image point. The measuring device comprises at least one measurement light source, an optical element group having at least one optical element and at least one capturing unit. The measurement light source emits at least one measurement light bundle, in particular a plurality of measurement light bundles, while the optical element group is adapted to guide the at least one measurement light bundle onto the at least one capturing unit in order to generate at least one capturing signal. In this case, thermal shielding is provided for the at least one optical element.

The present invention furthermore relates to an optical imaging device having an imaging unit for imaging an object point on an image point and a measuring device, the imaging unit having an optical element group with at least one optical element and the measuring device being adapted to determine state changes of the at least one optical element. The measuring device is adapted to determine the state changes of the at least one optical element during transport of the optical imaging device and register them in a log.

The present invention also relates to an optical imaging device having an imaging unit for imaging an object point on an image point, the imaging unit having an optical element group with at least one optical element. The imaging unit is adapted to image the object point on the image point by using light with a wavelength in the EUV range, particularly in the range of from 5 nm to 20 nm, and comprises a support structure having at least one structural element, by means of which the at least one optical element is supported. The at least one structural element comprises a material or a material combination having a coefficient of thermal expansion of more than $0.6 \cdot 10^{-6}$ $K^{-1}$, in particular more than $1.2 \cdot 10^{-6}$ $K^{-1}$.

Other preferred configurations of the invention are set forth in the dependent claims and in the following description of preferred exemplary embodiments, which refer to the appended drawings.

DETAILED DESCRIPTION OF EXEMPLARY EMBODIMENTS

First Embodiment

A preferred embodiment of the optical imaging device 101 according to the invention for microlithography will be described below with reference to FIGS. 1 to 4. To simplify the representation in the figures an xyz coordinate system, to which reference is made, is introduced in the figures.

Figure 1:
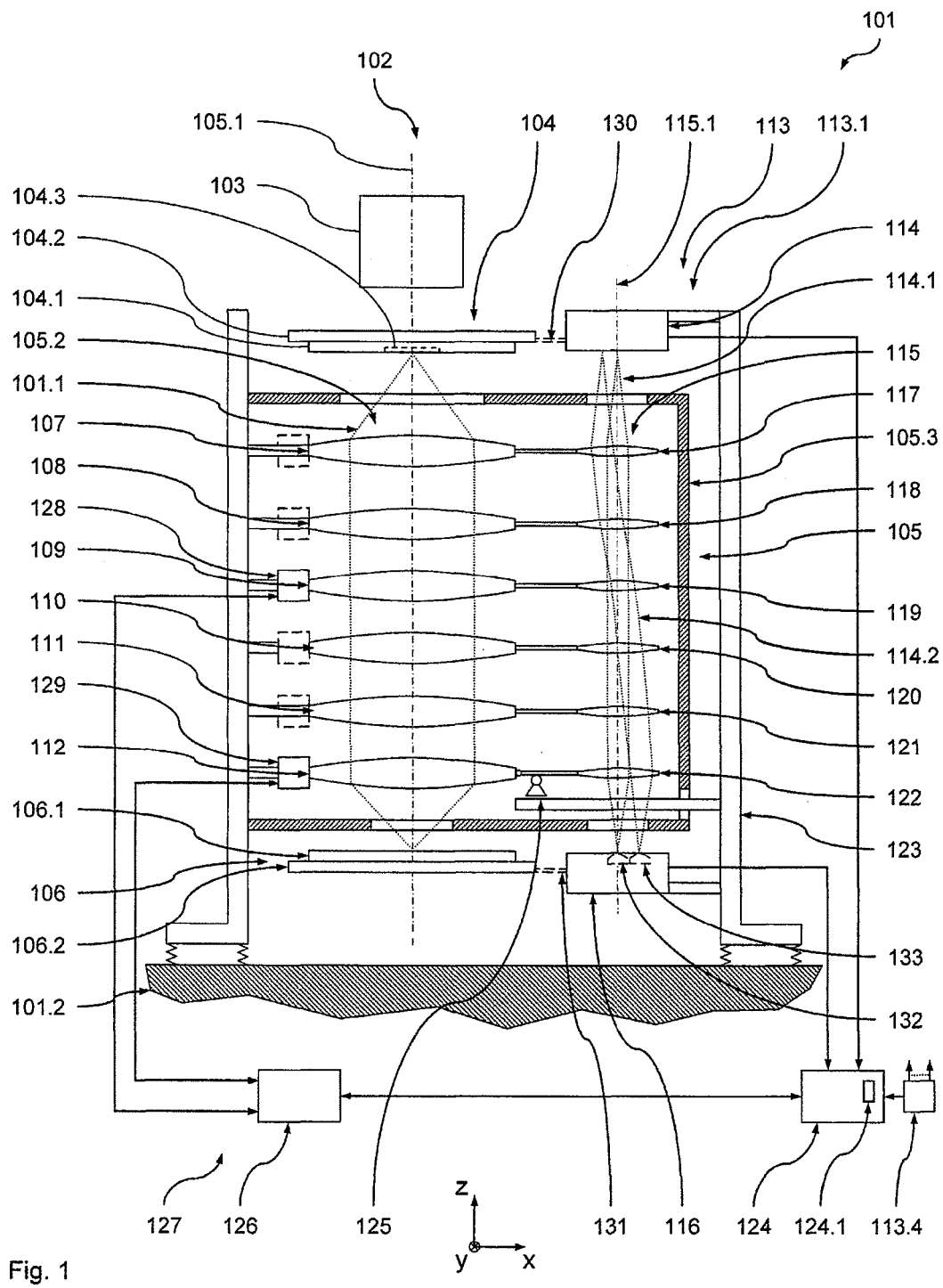
FIG. 1 is a highly schematised representation of a preferred embodiment of the optical imaging device according to the invention, with which a preferred embodiment of the imaging method according to the invention can be carried out.

FIG. 1 shows a highly schematised representation of the optical imaging device according to the invention in the form of a microlithography device 101, which operates with light having a first wavelength in the UV range. The microlithography device 101 comprises an imaging unit in the form of an optical projection system 102 having an illumination system 103, a mask device 104 and an optical device in the form of an objective 105 with an optical axis 105.1. The illumination system 103 illuminates the mask 104.1 of the mask device 104 with a projection light bundle 101.1 (not further represented in this section).

On the mask 104.1, which is arranged in a mask stage 104.2, there is a projection pattern 104.3 in an object plane (or more generally on an arbitrarily shaped object surface) having individual object points which are projected by the projection light bundle 101.1 via optical elements arranged in the objective 105 onto image points in an image plane (or more generally on an arbitrarily shaped image surface) on a substrate 106.1, for example a so-called wafer, of a substrate device 106.

To this end, the objective 105 comprises a first optical element group 105.2, which is formed by a plurality of first optical elements 107, 108, 109, 110, 111, 112 that are mounted in the housing 105.3 of the objective 105, which is in turn supported on a base structure 101.2. The first optical elements 107 to 112 project the projection light bundle 101.1 onto the substrate 106.1, and thus image an object point of the projection pattern onto an image point on the substrate 106.1.

A measuring device 113 is furthermore provided, with which (as will be explained in more detail below) an imaging error of the projection system 102 during imaging of the projection pattern of the mask 104.1 on the substrate 106.1 is determined. To this end, the measuring device 113 comprises a first measurement unit 113.1 having a measurement light source 114, a second optical element group 115 and a first capturing unit 116. The second optical element group 115 in turn comprises a plurality of second optical elements 117, 118, 119, 120, 121, 122, each of which is in a spatial relationship, defined at all times, with one of the first optical elements 107 to 112, as will be explained in more detail below.

In the example shown, the measurement light source 114 and the capturing unit 116 are rigidly connected to a reference structure 123, which is supported on the base structure 101.2. The reference structure 123, the measurement light source 114 and the capturing unit 116 are components which have been sufficiently stabilised thermally and mechanically, so that there is an accurately defined spatial relationship between the measurement light source 114 and the capturing unit 116 at all times. It is, however, to be understood that in other variants of the invention the spatial relationship between the measurement light source and the capturing unit may also be captured by means of a corresponding measurement technique (continuously or intermittently) and used in the course of determining the imaging error of the projection system 102.

In order to determine the imaging error of the projection system 102, the measurement light source 114 emits a measurement light bundle 114.1, which is guided or projected onto the capturing unit 116 via the second optical elements 117 to 122. As a function of the position and shape of the incident wavefront of the measurement light bundle 114.1, the capturing unit 116 generates a first capturing signal S1 which is delivered to a processing unit 124 of the measuring device 123. The processing unit 124 then uses this first capturing signal S1 in order to determine the imaging error of the projection system 102.

In preferred variants of the invention, in order to determine the imaging error of the projection system 102, the measurement light source 114 emits at least one further measurement light bundle in addition to the measurement light bundle 114.1, as is indicated in FIG. 1 by the measurement light bundle 114.2. The use of a plurality of measurement light bundles is known for example from WO 01/63233 A1 (Wegmann), the entire disclosure of which is incorporated herein by reference. This further measurement light bundle 114.2 is furthermore guided or projected onto the capturing unit 116 by means of the second optical elements 117 to 122. As a function of the position and shape of the incident wavefront of the further measurement light bundle 114.2, the capturing unit 116 generates a defined further first capturing signal S1 which is delivered to a processing unit 124 of the measuring device 113. The processing unit 124 then uses this further first capturing signal S1 in order to determine the imaging error of the projection system 102.

In other words, a plurality of measurement channels can be formed in the first measurement unit 113.1, by means of which the relevant imaging error or errors of the projection system 102 can be determined. For each measurement channel, a separate light source which generates the corresponding measurement light bundle 114.1 or 114.2 may be provided in the measurement light source 114. Likewise, the capturing unit 116 may have a plurality of separate sensors (for example one sensor per measurement channel). It is, however, also possible to provide a common sensor for a plurality of or even all of the measurement channels.

The measurements in the individual measurement channels of the first measurement unit 113.1 may be carried out in an arbitrarily predeterminable time sequence. The measurements in the individual measurement channels are preferably carried out chronologically synchronously (that is to say essentially simultaneously), since particularly reliable inferences about the respective imaging errors are thereby possible using the known correlation of the measurements from the individual measurement channels.

The second optical elements 117 to 122, as already explained above, are connected to the first optical elements 107 to 112 so that all times there is an accurately defined spatial relationship between the respective first optical element 107 to 112 and the second optical element 117 to 122 assigned to it. In the example shown in FIG. 1, for this purpose the respective second optical element 117 to 121 is connected directly and rigidly to the first optical element 107 to 111 assigned to it.

To this end, the respective optical element 117 to 121 may be fastened directly on a holding structure (for example a frame or a holding ring etc.) of the assigned first optical element 107 to 111 in order to ensure the spatial relationship, accurately defined at all times, between the second optical element 117 to 122 and the relevant first optical element 107 to 112. Likewise, it is possible for the second optical element 117 to 121 to be fastened (by a sufficiently stable suitable connection technique) directly on the assigned first optical element 107 to 111.

On the other hand, the second optical element 122 is connected to the associated first optical element 112 by means of a gearing device 125 supported on the reference structure 123. Depending on the configuration of the gearing device 125, a defined movement transmission takes place between a first movement of the first optical element 112 and the second movement, resulting therefrom, of the second optical element 122.

The effect which can then be achieved with the gearing device 125 (as represented in FIG. 1) is that a first movement of the first optical element 112 in a first degree of freedom causes a second movement of the second optical element in a second degree of freedom, which is different from the first degree of freedom. In this case, the type (translation or rotation) of the first and second degrees of freedom may optionally also differ. For example, a translation of the first optical element 112 along the z axis generates inter alia a rotation of the second optical element 122 about an axis parallel to the y axis.

As an alternative or in addition, an effect achievable using a corresponding configuration of the gearing device 125 is moreover that the movements of the first optical element 112 and of the second optical element 122 take place in the same degree of freedom. In the case of the gearing device 125 of FIG. 1, for example, a translation of the first optical element 112 along the x or y axis generates an identical translation of the second optical element 122 along the x or y axis, respectively. Likewise, a rotation of the first optical element 112 about an axis parallel to the y or z axis results in a rotation of the second optical element 122 about an axis parallel to the y or z axis, respectively.

The gearing device 125 may in principle be configured in any desired suitable way. For instance, it may be configured in one part or a plurality of parts. A suitable number of lever elements and articulations connecting them may be provided. Preferably, the respective articulations are configured as solid-state articulations (flexural articulations, leaf spring elements etc.) in order to minimise the effects of manufacturing inaccuracies (for example undesired play) and readily ensure the spatial relationship, defined at all times, between the first and second optical elements.

In the example shown in FIG. 1, the second optical elements are furthermore arranged so that the optical axis 115 defined by them extends in the direction of the optical axis 105.1. Accordingly, with rigid coupling, a translation of the first optical elements 107 to 111 in the direction of the z axis is converted into a translation of the second optical elements 117 to 121 in the direction of the z axis. It is, however, to be understood that in other variants of the invention the directions of respective optical axes may also differ at least for individual optical elements.

The effect achieved by the mechanical coupling defined at all times between the respective first optical elements 107 to 112 and the associated second optical elements 117 to 122 is that a state change (here a change in position and/or orientation) of the respective first optical element 107 to 112 necessarily entails a corresponding state change (position and/or orientation) of the assigned second optical element 117 to 122.

The state changes of the second optical elements 117 to 122 in turn entail a change in the imaging properties or aberrations of the second optical element group 115, which lead to a modification of the geometry and/or position of the wavefront of the measurement light bundle 114.1 incident on the capturing unit 116. This in turn entails a change in the first capturing signal S1, which the capturing unit 116 delivers. A suitable measurement technique of the capturing unit 116 can thus capture the change in the imaging properties of the second optical element group, for example the modification of the incident wavefront, with one or more wavefront sensors at one or more field points.

Various known arrangements and principles may be employed for the wavefront measurement. These include inter alia interferometers (Michelson, Twyman, Green, shearing, point diffraction interferometers etc.). These also include wavefront sensors which are based on segmenting the pupil (i.e. dividing it into sub-pupils) and determining the positions or position changes of the focal positions of the bundles from the sub-pupils. Examples of this are sensors of the Hartmann, Shack-Hartmann type etc.

Another type sensor which may be used operates according to a measurement method which is referred to as phase retrieval (from a point image) (the so-called "phase retrieval measurement technique" or "aerial image measurement technique"). In this case, the corresponding phase distribution in the pupil is calculated from the three-dimensional intensity distribution in the region of the respective point image of the measurement image. In order to acquire the three-dimensional intensity distribution, a two-dimensional sensor (for example a camera which acquires a plane intensity distribution) is moved through the focal region or the beam waist in the third dimension (transversely to the measurement plane of the sensor). The capturing of the intensity distribution thus takes place stepwise. The wavefront in the exit pupil can then be calculated back from this image stack obtained in this way (using so-called "phase retrieval algorithms").

It is furthermore to be understood that the state change to be detected of the second optical elements 117 to 122 may possibly also impact on simpler measurement quantities of the measuring device 113, for example on a lateral image offset or a focal change. In this case, measurement techniques other than a wavefront measurement technique may be provided, for example focal sensors (change in the focal position along the optical axis) or moiré techniques as sensors for the offset of the image position or the change of scale and/or distortion of the measurement optics. Naturally, combinations of wavefront sensors and position sensors are also possible.

Using a previously determined model of the measuring device 113, stored in the processing unit 124, the state changes (position and/or orientation) of the second optical elements 117 to 122 can be deduced with the aid of the measurement data of the wavefront sensors. The model of the measuring device 113 may have been determined beforehand theoretically (for example by corresponding simulation calculations) and/or experimentally (for example via corresponding calibration) for the measuring device 113. The model of the measuring device 113 gives the relationship between the measurement data of the wavefront sensors and the respective state changes of the second optical elements 117 to 122.

Owing to the above-described defined coupling between the first optical elements 107 to 112 and the second optical elements 117 to 122, the processing unit 124 in turn determines the corresponding state changes of the first optical elements 107 to 112 from the state changes of the second optical elements 117 to 122.

From these state changes of the first optical elements 107 to 112, using the previously determined model of the first optical element group 105.2 stored in the processing unit 124, the processing unit 124 determines the current imaging properties or current imaging errors of the first optical element group 105.2. The model of the first optical element group 105.2 may have been determined beforehand theoretically (for example by corresponding simulation calculations) and/or experimentally (for example by means of corresponding calibration) for the first optical element group 105.2. The model of the first optical element group 105.2 gives the relationship between the state changes of the first optical elements 107 to 112 and the respective imaging errors.

The processing unit 124 then forwards the respective currently determined imaging errors to a control device 126 of a correction device 127. From the currently determined imaging errors of the first optical element group 105.2, the control device 126 determines control signals for actuator devices 128 and 129. The actuator devices 128 and 129 are connected to individual first optical elements 109 and 112, respectively, and are used in a well-known way to modify the position and/or orientation and/or geometry of the respective first optical element 109 or 112 in order to reduce the currently determined imaging error.

The coupling with a spatial relationship defined at all times, between the first optical elements 107 to 112 and the second optical elements 117 to 122 of the measuring device 113 affords the advantage that the determination and correction of the imaging error can take place in real time during the actual exposure of the substrate 106.1, without thereby interfering with the process of exposing the substrate.

In the present example, merely two actuator devices 128 and 129 are provided. It is, however, to be understood that in other variants of the invention any other desired number of actuator devices may be provided. In particular, each first optical element 107 to 112 may be provided with a corresponding actuator device (as indicated in FIG. 1 by the corresponding dashed outlines).

The measuring device 113 is preferably configured so that the changes in the imaging properties of the second optical element group 115, and therefore the changes in the measurement data of the wavefront sensors, can be assigned as unequivocally as possible to particular state changes of the individual second optical elements 117 to 122. In this case, particularly by using one or more gearing devices 125, it is possible to convert the movement of a first optical element into a movement of the associated second optical element, which increases the uniqueness of the assignment of the changes in the measurement data to the state changes of the individual second optical elements 117 to 122. In particular, the change achievable by such a gearing device in the type of degree of freedom (translation or rotation) may be of considerable advantage here.

The sensitivity of the measuring device 113 for all degrees of freedom of the second optical elements 117 to 122 relevant to the present case is known from the configuration of the measuring device 113 (for example, the change in the Z7/Z8 coma centring and the Z5/Z6 astigmatism centring corresponds to the ratio 4:1 for a translation of optical elements) and correspondingly saved in the stored model of the measuring device 113.

In the event of poor conditioning of the second optical element group 115 (for example low sensitivity, uniqueness, separability or orthogonality of the equation system of the sensitivity to state changes of the individual second optical elements) the conditioning can be improved by the addition of extra optical element groups. To this end, for example, an identical (to the second optical element group 115) third optical element group may be linked to a different position (for example rotated through 90° or 180° with respect to the z axis) on the first optical element group in an identical or similar fashion. It is likewise possible to achieve optimisation of the conditioning of the measuring device 113 by controlled optimisation of the configuration and coupling of two or a plurality of mutually differing optical element groups to the first optical element group 107 to 112, as will further be described below in connection with FIGS. 2 and 3.

The measuring device 113 may in particular be configured so that its sensitivity corresponds to the sensitivity of the projection system 102, or at least so that there is a simple (for example proportional) relationship between these sensitivities. In this context, by suitable selection of the movement transmission, the gearing device 125 makes it possible to adapt the sensitivity of the measuring device 113 to the measurement task in question.

Such adaptation of the sensitivity of the measuring device 113 by means of one or more gearing devices may, for example, be advantageous when an imaging error of the projection system 102 is more sensitive to a state change of one or more of the first optical elements 107 to 112 than the measuring device 113 is to a state change of the assigned second optical element 117 to 122. The sensitivity of the measuring device 113 can then be suitably increased in a straightforward way by the movement transmission. In particular, the effect achievable by the movement transmission is that the sensitivity of the measuring device 113 to a state change of one of the second optical elements 117 to 122 reaches or even exceeds the sensitivity of an imaging error of the projection system 102 to a state change of the associated first optical element 107 to 112.

Furthermore, in this context it may also be advantageous to convert the translation of a first optical element 107 to 112 into a rotation of the assigned second optical element 117 to 122 with such a gearing device. Lastly, such gearing devices may be necessary in order to accommodate other constraints (and available installation space, distances to be covered etc.

Since it is possible that the kinematics and sensitivity of the measuring device 113 cannot be theoretically modelled or practically implemented well enough, or variations have to be taken into account, calibration of the measuring device 113 may as mentioned be necessary in order to compile or adapt the model. For such calibration, the objective 105 may initially be optimised with a system interferometer, i.e. all the components may for example be brought into their setpoint state (setpoint position, setpoint orientation and setpoint geometry) using corresponding manipulators. Here, the setpoint state refers to a state in which the aberrations cause the minimal achievable deviation from an ideal state. The ideal state depends on various parameters of the imaging, for example the shape and the dimension of the structures to be imaged, the illumination setting, the size of the imaging field used etc.

After the setpoint state has been achieved, the capturing units of the measuring device 113 (i.e. for example its sensors, measurement transducers etc.) are "zeroed" (i.e. their intrinsic error is set to "zero"). This state is then also the setpoint state for the regulation of the correction of the imaging errors during operation of the microlithography device 101. The sensitivities of the optical elements of the measuring device 113 to position changes of the components of the projection device 102 (in particular of the first optical elements 107 to 112) are then determined by controlled (continuous or stepwise) adjustment of the actuators of the projection device 102, in order to determine a sensitivity curve. The sensitivity curves determined in this way are then saved in a model, or in a sensitivity matrix, so that the actuator movements necessary for the correction of the imaging errors can be determined and instigated during control operation from the measurement data of the measuring device 113.

In the present example, the static reference structure 123 is used as a reference for the measuring device 113. It is, however, to be understood that in other variants of the invention a relative (optionally mobile) reference may be expedient. This may in particular be advantageous if the desired measurement quantity comprises a relative position, for example the position of the mask device 104 relative to the substrate device 106. In this case, a particular reference region of the objective 105 may be expedient as the reference of the measuring device.

The measurement light source and/or the capturing unit may also be connected not to the reference structure 123 but to the mask device 104 or substrate device 106, as indicated in FIG. 1 by the dashed outlines 130 and 131. Here, the connection may be carried out similarly to the manner described above for the connection between the first and second optical elements (directly rigidly or via a gearing device), so in this regard reference is made to the comments above.

The measurement light source and the capturing unit may furthermore be arranged next to one another, and optionally even integrated in a single unit, in order to establish a defined spatial relationship between them in a straightforward way. In the embodiment of FIG. 1, a reflective element, for example a mirror or the like, would then merely need to be arranged for example at the position of the capturing unit 116, as indicated in FIG. 1 by the dashed outline 132.

In order to be able to capture state changes of the mask device 104 or the substrate device 106 as well, in other variants of the invention, they may also be coupled to a corresponding second optical element in a similar way as the first optical elements 107 to 112.

The measuring device may (as mentioned above) be equipped with a plurality of measurement channels or measurement principles, in order very rapidly to detect deviations in all six degrees of freedom and make them available for rapid regulation. For example, moiré channels may be provided for translations in the direction of the x and y axes and a rotation about the z axis, while rapid focal detection may be provided for translation in the direction of the z axis and a rotation about the x and y axes.

As already mentioned, FIG. 1 shows a highly schematised representation of the imaging device 101, in which the first and second optical elements are represented schematically by lenses (for the sake of simpler representation). It is, however, to be understood that the first optical elements 107 to 112 and the second optical elements 117 to 122 may be formed individually or in any desired combination by refractive, diffractive and reflective optical elements. In particular, these optical elements may have any desired suitable geometry. For instance, elements with spherical, aspherical, cylindrical, plane optical surfaces or freeform surfaces may be used as optical surfaces.

In the case of the second optical elements 117 to 122, the geometry of the optical elements may be adapted to the measurement result to be achieved. Thus, the effect achievable by a different configuration of the optical surfaces of the second optical elements 117 to 122 along different degrees of freedom (for example a different curvature along different degrees of freedom) is that the movements along these different degrees of freedom result in different changes in the capturing signals of the capturing unit 116, which allow correspondingly unequivocal inference of the associated state changes of the respective second optical elements 117 to 122.

For example, the geometry of the second optical element (as for example in the case of the optical element indicated by the dashed contour 132 in FIG. 1) may contribute to simple discrimination of state changes. In a variant with two or more measurement channels (for example with the two measurement light sub-bundles 114.1 and 114.2) and two such (convex or concave) mirrors 132, 133 correspondingly arranged next to one another, a translation of the mirror 132, 133 along the x axis or the y axis causes equally large tilting of the returning waves in both measurement channels, and a translation along the z axis likewise causes equally large defocusing. A rotation about the z axis, however, causes unequal tilting of the waves while a rotation about the x axis causes unequal defocusing of the waves.

In the present example, each of the first optical elements 107 to 112 is coupled to precisely one second optical element 117 to 122. It is, however, to be understood that in other variants of the invention only some of the first optical elements 107 to 112 may respectively be coupled to one or more of the second optical elements. In particular, a state capturing of sufficiently (thermally and mechanically) stable first optical elements may possibly be dispensed with.

As already mentioned above, in the event of insufficient conditioning of the second optical element group 115, the conditioning may be improved by adding extra optical element groups. In the microlithography device 101, this is done by a third optical element group 134 of the measuring device 113, as will be explained below with reference to FIGS. 2 and 3.

Figure 2:
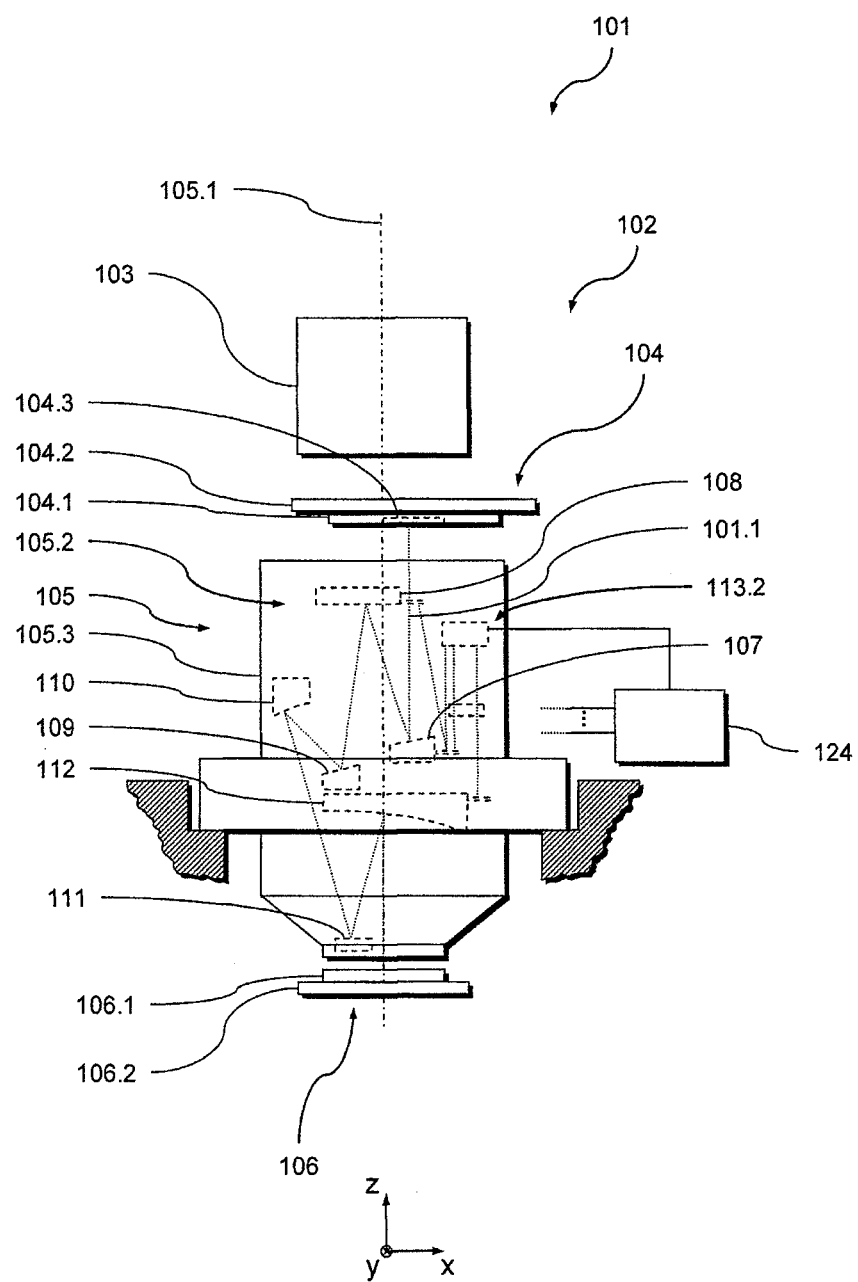
FIG. 2 is a more concrete schematic representation of the imaging device of FIG. 1.
Figure 3:
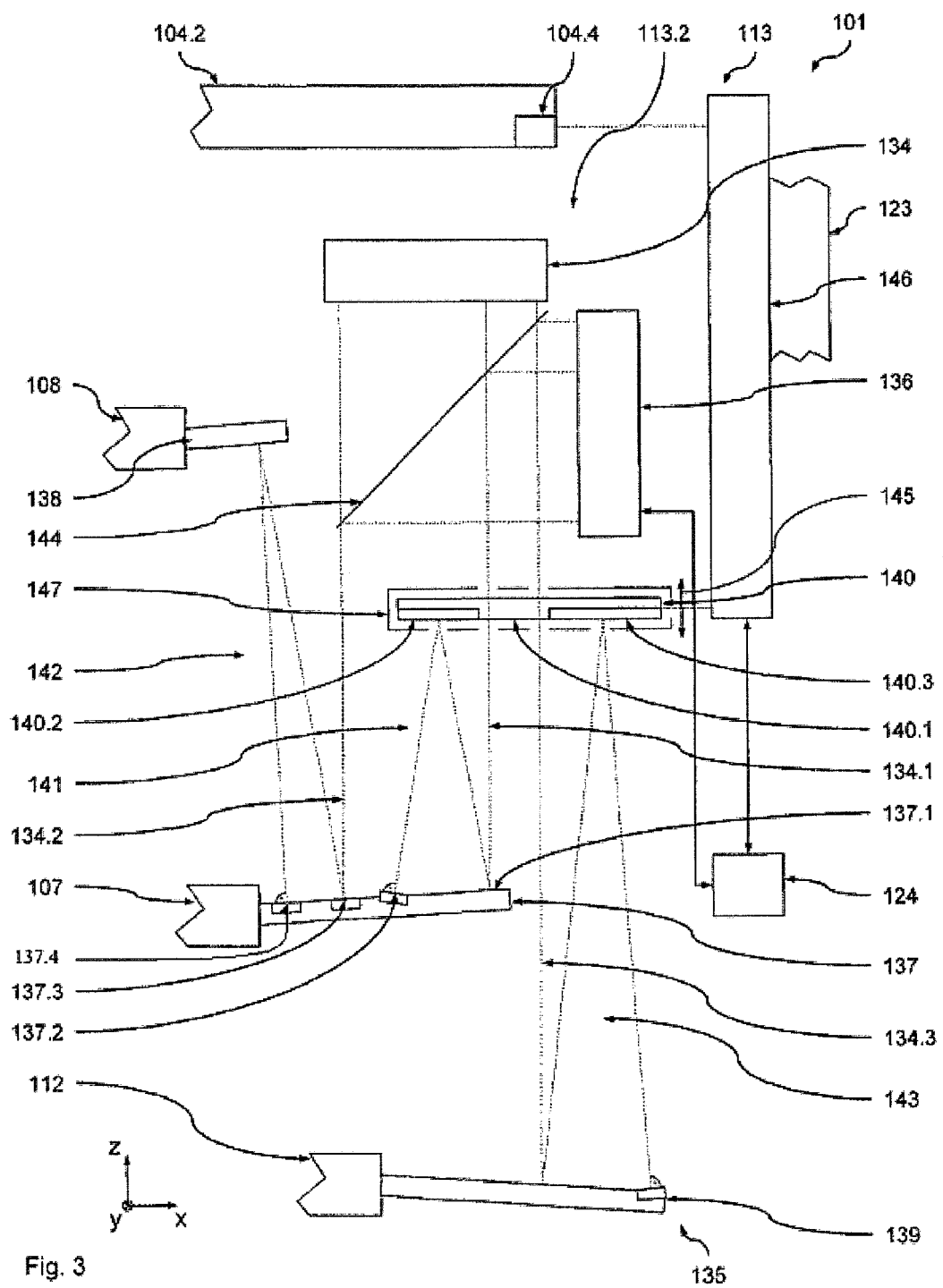
FIG. 3 is a schematic representation of a part of the imaging device of FIG. 1.

FIG. 2 shows a (compared with FIG. 1) more concrete configuration of the microlithography device 101, which operates with a projection light bundle 101.1 in the EUV range with a wavelength of 13.5 nm. For this reason, the first optical elements 107 to 112 in this embodiment are formed exclusively as reflective optical elements in the form of mirrors. FIG. 3 shows a schematic detail of the microlithography device 101 of FIG. 2.

As already mentioned in the introduction, reliable detection of wavefront tilts of $\lambda/1000$ over a predetermined measurement aperture is for example possible with a usual interferometric measurement. If this measurement aperture has a diameter of 100 mm, for example, then this corresponds to an angular resolution of 6 nrad when the measurement wavelength $\lambda$ is the wavelength of a conventional helium-neon laser.

The image position during a current process of exposing the substrate 106.1 must remain within the scope of specified limits. As mentioned, the beam path in an EUV objective 105 may be a several meters long. With structures to be exposed of the order of 25 nm, however, the image displacements must only lie in the nanometer range. A length of about 2.5 m for the beam path of the projection light bundle 101.1 (between the mirror 107 and the substrate 106.1) and an admissible image displacement of 1 mm entail a maximum admissible mirror tilt of only 0.2 nrad for the mirror 107. Although these angular tolerances increase stepwise for the subsequent mirrors 108 to 112 in the beam path, since their distance from the image plane (i.e. from the substrate 106.1) decreases continuously, here again angular tolerances in the sub-nrad range should ideally be complied with as before.

In order to achieve this, according to an aspect of the present invention a time-resolved measurement of the orientation of the mirrors 107 to 112 in the sub-nrad range by the measuring device 113 is provided, with the aid of which image position changes can be identified in real time in parallel with the exposure of the substrate 106.1 and corrected by the correction device 127.

This will be described below by way of example with the aid of the mirrors 107, 108 and 112. Since tilts (as changes in orientation) of all the mirrors 107 to 112 can contribute to the image displacement, albeit to a different extent, it is preferable for the tilts of all the mirrors to be observed and corrected in this manner described below.

For this purpose, the measuring device 113 comprises an interferometric second measurement unit 113.2 having a second measurement light source 134, a third optical element group 135 and a second capturing unit 136. Besides a row of reflective third optical elements in the form of measurement mirrors 137, 138 and 139, the third optical element group 135 has a partially reflective optical reference element 140. The third optical elements 137, 138 and 139 in the present example are respectively coupled to one of the mirrors 107, 108 and 112, in such a way that there is a spatial relationship, defined at all times, between the mirror 107, 108 and 112 and the associated, respective third optical element 137, 138 and 139. To this end, the coupling between the third optical elements 137, 138 and 139 and the first optical elements 107, 108 and 112 may be configured in a similar way to the coupling described above of the first optical elements 107 to 112 and the second optical elements 117 to 122 (i.e. directly rigidly and/or through gearing devices). In the present example, the third optical elements 137, 138 and 139 are connected rigidly to the respective mirror 107, 108 and 112.

The resolution in the sub-nrad range when measuring the orientation of the mirrors 107 to 112 is achieved by forming an optical cavity in the manner of a Fizeau cavity between the measurement mirrors 137, 139 and the reference element 140, and respectively between the measurement mirror 137 and the measurement mirror 138. This cavity is passed through a plurality of times because the optical elements 137 to 140, which form the respective optical cavity 141, 142 and 143, are arranged so that a measurement light bundle input into the cavity (at the optical elements 137 to 140 forming the respective cavity) experiences a plurality of M reflections before it leaves the cavity again and strikes the second capturing unit 136. Owing to these M reflections, angular deviations between the two optical elements 137 to 140 forming the cavity are multiplied, so that an angular resolution in the sub-nrad range can readily be achieved even with the aforementioned simple interferometric measurement.

For this purpose, the second measurement light source 134 emits inter alia a measurement light bundle 134.1 which travels to the reference element 140 via a beam splitter 144. The incident measurement light bundle 134.1 passes through the partially reflective reference element 140 and on the exit side it is partially reflected on a surface region 140.1 of the optical reference surface so that a returning reference wave is formed. The transmitted fraction passes through the optical cavity 141 formed between the reference element 140 and the first measurement mirror 137, and is reflected on a first surface region 137.1 of the measurement mirror 137.

The surface normals of the reference surface 140.1 and of the first surface region 137.1 (in a setpoint state) are arranged mutually inclined so that the measurement light bundle 134.1 (in this setpoint state) is not folded back on itself. From the first surface region 137.1, the measurement light bundle 134.1 is reflected back inside the cavity 141 to the reference body 140, strikes a preferably totally reflective surface region 140.2 and is reflected again there. The measurement light bundle 134.1 passes through the cavity 141 again and strikes a surface region 137.2 of the first measurement mirror 137 perpendicularly. In this way, the measurement light bundle 134.1 is folded back on itself so that it returns along essentially the same path in order to leave the cavity 141 again in the partially reflective region of the surface region 140.1 of the reference element 140. The measurement light bundle 134.1 is then guided using the beam splitter 144 onto the capturing unit 136, where it leads to the generation of a second capturing signal S2 which is representative of the angular deviations between the first measurement mirror 137 and the reference element 140 and therefore (owing to the coupling which is defined at all times) of a current angular deviation of the first optical element 107 (from a setpoint state).

The capturing signal S2 is forwarded to the processing unit 124, which then uses the capturing signal S2 in the manner described above in order to determine the imaging errors of the projection device 102 and correct them with the correction device 127.

Depending on the application, the M=5 reflections inside the cavity 141 as represented in FIG. 3 may still not be sufficient in order to achieve the angular resolutions required above in the sub-nrad range. It is, however, to be understood that any desired number of reflections inside the cavity 141 can be achieved through simple selection of the alignment of the optical surfaces 137.1, 140.2 and 137.21 forming the cavity 141. At least 21 reflections are preferably provided when passing through the cavity.

If the angular deviation between the first measurement mirror 137 and the reference element 140 is so small that the reflected rays of the measurement light bundle 134.1 overlap with the incoming measurement rays on the reference element 140, they will be partially transmitted and travel back to the capturing unit 136 where they can be captured by an aperture device at the intermediate focus of the capturing unit 136.

For the relative shift of the phases of the measurement wave and the reference wave, with a view to a phase-shifting interference evaluation, the reference element 140 may be displaceable along the direction 145 by suitable actuators. As an alternative, a phase shift using a wavelength shift is also possible. If this is intended to be avoided, the widely known so-called DMI method may furthermore be used, as is known from U.S. Pat. No. 5,361,312 (Küchel), the entire disclosure of which is incorporated herein by reference. The cavity 141 can thus be formed so that a carrier frequency appears in the interferogram of the capturing unit 136 and is subsequently eliminated computationally (in the capturing unit 136 or the processing unit 124).

In a similar way, using a further measurement light beam 134.3 and the cavity 143 formed between the reference element 140 and the third measurement mirror 139, angular deviations between the third measurement mirror 139 and the reference element 140 are determined and used in order to determine and correct the imaging error of the projection device 102.

The second measurement light source 134 furthermore emits a measurement light bundle 134.2 that enters the optical cavity 142 which is formed between the first measurement mirror 137 and the second measurement mirror 138. The measurement light bundle 134.2 initially strikes a diffractive element in the form of a grating 137.3 in so-called Littrow arrangement. By means of the grating 137.3 on the first measurement mirror 137, on the one hand a returning reference wave is generated. The specular reflection of the measurement light bundle 134.2 at the grating (zero-th diffraction order) passes through the cavity 142 a plurality of times in a similar way to that described above (in connection with the measurement light bundle 134.1 and the cavity 141), until it strikes the surface region 137.4 of the first measurement mirror 137 perpendicularly and is reflected back on itself. The measurement light bundle 134.2 then travels back along essentially the same path before leaving the cavity 142 again through the grating 137.3. Here, angular deviations (from a setpoint state) between the first measurement mirror 137 and the second measurement mirror 138 are again added using the number of reflections inside the cavity 142.

The measurement light bundle 134.2 is then guided by the beam splitter 144 onto the capturing unit 136, where it leads to the generation of a third capturing signal S3 which is representative of the angular deviations between the first measurement mirror 137 and the second measurement mirror 138 and therefore (owing to the coupling which is defined at all times) of a current angular deviation of the first optical elements 107 and 108 (from a setpoint state).

For phase shifting, one of the two measurement mirrors 137 and 138 may again be mounted displaceably. If this is intended to be avoided (with a view to the defined coupling with the relevant first optical element 107, 108), here again either so-called wavelength tuning may be used or the aforementioned DMI method may be used.

As already mentioned, the reference element 140 and the measurement mirrors 137 to 139 preferably have locally varying reflectivities. The surface region 140.1 of the reference element 140, which generates the reference wave by partial reflection, may for example have a reflectivity of about 40% while the other surface regions 140.2 and 140.3 have a high reflectivity of for example almost 100%. The surface regions 137.1 and 137.2 of the first measurement mirror 137 may likewise have a high reflectivity. In this case, the reference wave and the measurement wave have comparable intensities, so that a high contrast of the interference pattern in the region of the capturing unit 136 is advantageously ensured.

As can be seen in FIG. 3, determination of the lateral displacement (deviation in the x direction and y direction) of the objective 105 with respect to the mask stage 104.2 is furthermore provided in the present example, since this displacement affects the lateral image position in the image plane (i.e. on the substrate 106.1). To this end a mask reference body 104.4 is arranged on a non-actuated, i.e. stationary, region of the mask stage. A position measurement unit 146 (formed in a well-known way) linked to the reference structure 123 captures the spatial relationship between the reference body 104.4 and the reference element 140 and forwards corresponding information into the processing unit 124 for further processing in the determination of the imaging error. The resolution of the position measurement unit 146 is of the order of the admissible image displacements, i.e. in the nanometer range in the present example.

It is to be understood that by corresponding extensions of the second measurement unit 113.2, or by further measurement units, it is also possible to capture the angular deviations of the three other first optical elements 109 to 111 (absolutely or relative to one another). In particular, according to an aspect of the present invention, it is possible to determine all angular deviations relative to a single reference body, namely the reference element 140, and additionally to capture the position of the entire objective 105 relative to the mask unit 102 in real time in parallel with the exposure of the substrate 106.1. All these quantities are advantageously related to a single common reference body 140.

The reference element 140 is therefore preferably made of a material or a material combination having a low coefficient of thermal expansion (CTE). Materials such as Zerodur, ULE, quartz glass or the like may in particular be used for the partially transmissive part of the reference element 140. The reference element is preferably configured so that it has an aspect ratio of less than 7, in particular an aspect ratio of less than 3, in order to avoid bending.

The reference element 140 is preferably provided with a thermal heat shield in the form of a radiation protection shield 147, in order to thermally stabilise it. The radiation protection shield 147 may for example be a metal foil or a metal shell with openings for the respective measurement light bundle. Optionally, the radiation protection shield 147 may be cooled actively and/or passively. In particular, temperature regulation may also be provided in order to keep the protective shield 147 at a constant temperature.

In this context, it should be mentioned that the provision of such a thermal protection shield for optical elements of the measuring device constitutes a separately protectable inventive concept which is independent from the rest of the configuration of the measuring device.

Another advantage of the measuring device 113 according to the invention is that changes in the angular deviations of the measurement mirrors 137 to 139 result in a change in the interference fringe spacing in the interferogram of the capturing unit 136, and after phase-shifting evaluation also result in a change of the wavefront tilt coefficient. Whereas translational changes of the measurement mirrors 137 to 139 along the respective measurement light bundle 134.1 to 134.3 merely result in a change of the interference fringe positions in the interferogram of the capturing unit 136, after the phase-shifting evaluation they thus result in a change of the offset. In this way, in addition to capturing the changes of the angular deviations is also possible to capture translational changes of the measurement mirrors 137 to 139 along the respective measurement light bundle 134.1 to 134.3.

In a preferred embellishment to the present embodiment, the measuring device 113 is configured to be transportable together with the objective 105, and the measuring device 113 continues to be operated (in a logging step) during transport of the objective 105. To this end, for example, a mobile electricity supply 113.4 (such as a battery or an accumulator etc.) may be provided, which supplies the electrically operated components of the measuring device 113, in particular the processing unit 124, with electrical energy. The respective interferograms of the measuring device 113 are captured continuously or at regular time intervals, and optionally stored in a suitable form in a memory 124.1 of the processing unit 124. After transport, the state changes (geometry and/or position and/or orientation) of the first optical elements 107 to 112 can thus be reproduced (in an analysis step) with the aid of the data read out from the memory 124.1, and a corresponding correction can be carried out straightforwardly (in a correction step).

In this context, it should be noted that the mobile capturing of state changes of the optical elements of a projection system constitutes a separately protectable inventive concept which is independent from the type of capturing of the state changes or the configuration of the measuring device used.

Figure 4:
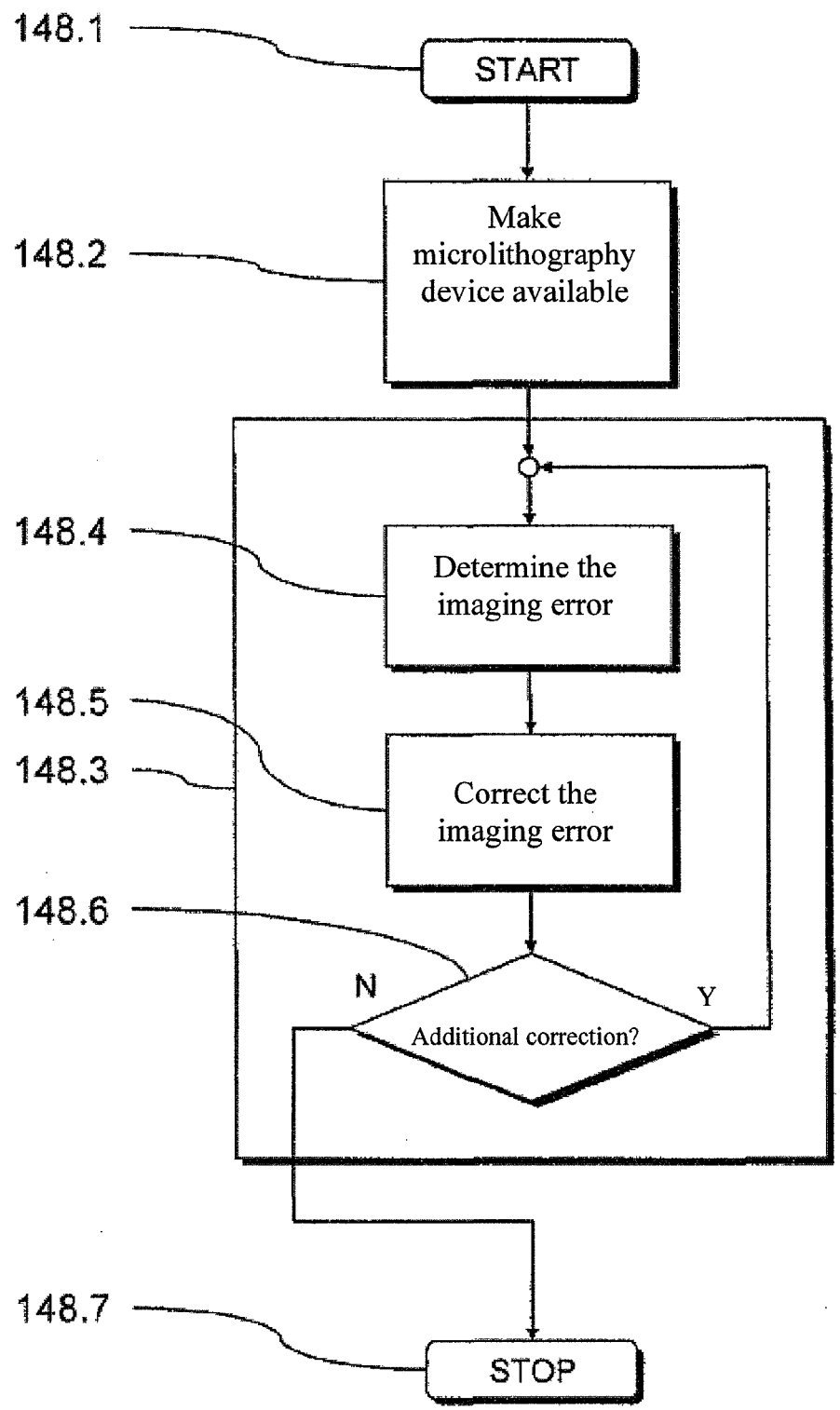
FIG. 4 is a flow chart of a preferred embodiment of the imaging method according to the invention, which can be carried out with the imaging device of FIG. 1.

FIG. 4 shows a flow chart of a preferred embodiment of the imaging method according to the invention in the form of a microlithography method, which is carried out with a microlithography device 101 of FIGS. 1 to 3 operating according to the so-called scanner principle.

First, in a step 148.1, the method flow of the microlithography method is started. In a step 148.2, the microlithography device 101 is then made available in the configuration of FIGS. 1 to 3.

In a capturing and correction sequence 148.3 of steps, a determination of the imaging error is initially carried out in a determination step 148.4 in parallel with the exposure of the substrate 106.1. To this end, as described in connection with FIGS. 1 to 3, the capturing signals S1 to S3 are generated by the measurement units 113.1 and 113.2 of the measuring device 113, and processed in the processing unit 124.

As a function of the imaging error thereby determined in the imaging of the projection pattern 104.3 on the substrate 106.1, the correction of the respective imaging error as described above in connection with FIGS. 1 to 3 is then carried out by the correction device 127 in the correction step 148.5, by the control device 126 correspondingly driving the actuators 128, 129 in the first optical elements 109 and 112.

As mentioned, the determination and correction of the imaging error are carried out in parallel with the exposure of the substrate 106.1. At least so long as no imaging errors are captured, which would necessitate an interruption to the exposure of the substrate 106.1, the exposure thus takes place simultaneously with and/or independently of the determination and correction of the imaging error.

In a further step 148.6, a check is then made whether a further correction process should still be carried out. If this is not the case, the method flow ends in step 148.7. Otherwise, it returns to step 148.4.

Owing to the highly precise capturing and correction of the imaging errors of the projection system 102 taking place in real time in parallel with the exposure of the substrate 106.1, in one aspect of the present invention it is possible to make the structural components of the microlithography device, which in respect of the imaging errors of the projection system 102 have a substantial influence on the state (geometry and/or position and/or orientation) of the optical elements of the imaging system, i.e. in particular the support structure for the first optical elements 107 to 112, entirely or partially from thermally more sensitive materials (i.e. for example materials having a comparatively high coefficient of thermal expansion), since thermally induced perturbations that lead to imaging errors can readily be compensated for.

In particular, in the case of an EUV system (typically with a working wavelength of from 5 nm to 20 nm), in contrast to the previously known systems it is sometimes even possible to use thermally comparatively sensitive but economical materials such as Invar or the like for these structural components. It is thus possible to use for these structural components materials or material combinations the coefficient of thermal expansion (CTE) of which is close to or more than the coefficient of thermal expansion of Invar, i.e. in particular more than $0.6 \cdot 10^{-6}$ $K^{-1}$, in particular even more than $1.2 \cdot 10^{-6}$ $K^{-1}$.

In this context, it should be noted that this capturing and correction of state changes of the optical elements supported by such thermally more sensitive materials of a projection objective operating in the EUV range, in parallel with the exposure of the substrate, constitutes a separately protectable inventive concept which is independent of the type of capturing of the state changes or the configuration of the measuring device used.

Second Embodiment

Figure 5:
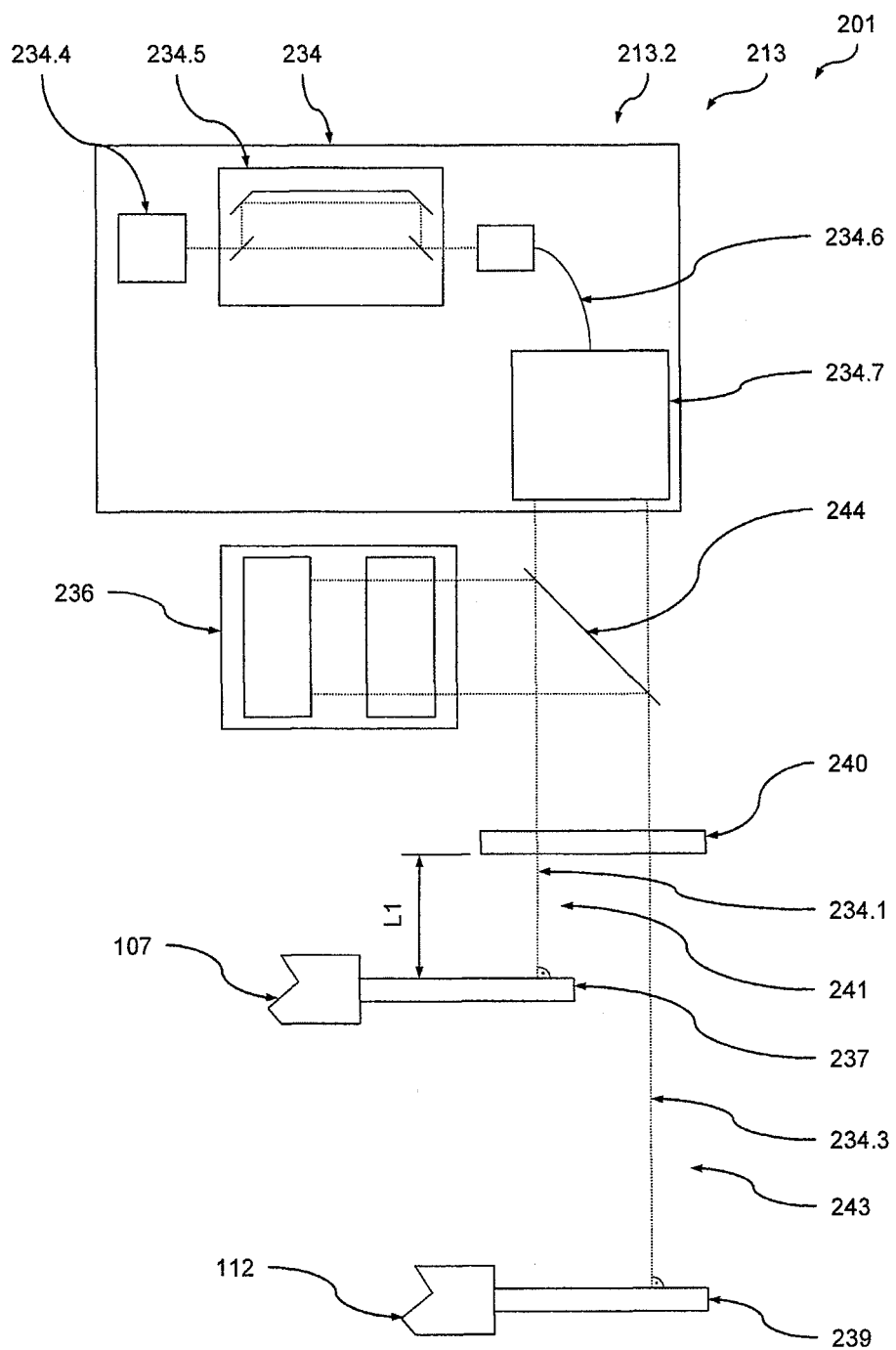
FIG. 5 is a schematic representation of a part of another preferred embodiment of the imaging device according to the invention.

Another preferred embodiment of the microlithography device 201 according to the invention will be described below with reference to FIG. 5. FIG. 5 shows a detail of the microlithography device 201, which corresponds to the detail of FIG. 3.

Basically, the microlithography device 201 corresponds in structure and functionality to the microlithography device 101 of FIGS. 1 to 3, so merely the differences will be discussed here. In particular, components of the same type are provided with references augmented by the value 100. Unless otherwise mentioned below, reference should be made to the comments above in connection with the first embodiment with respect of the properties of these components.

The only material difference of the microlithography device 201 from the microlithography device 101 consists in the configuration of the second measurement unit 213.2. In the microlithography device 201 as well, a time-resolved measurement of the orientation of the mirrors 101 to 112 is carried out in the sub-nrad range, with the aid of which image position changes can be identified in real time in parallel with the exposure of the substrate 106.1 and corrected via the correction device 127.

This will be described below by way of example with the aid of the mirrors 107 and 112. Since tilts (as changes in orientation) of all the mirrors 107 to 112 can contribute to the image displacement, albeit to a different extent, it is preferable for the tilts of all the mirrors to be observed and corrected in this manner described below.

In the case of the second measurement unit 213.2, the resolution in the sub-nrad range when measuring the orientation of the mirrors 107 to 112 is again achieved by forming an optical cavity 241 and 243 in the manner of a Fizeau cavity between the measurement mirrors 237 and 239, respectively, and the reference element 240. These cavities 241 and 243 are passed through a plurality of times because the optical elements 237, 239 and 240, which form the respective optical cavity 241 or 243, are arranged so that a measurement light bundle input into the cavity (at the optical elements 237, 239 and 240 forming the respective cavity) experiences a plurality of M reflections before it leaves the cavity again and strikes the second capturing unit 236. Owing to these M reflections, angular deviations between both the optical elements 237, 239 and 240 forming the cavity are multiplied, so that an angular resolution in the sub-nrad range can readily be achieved even with the aforementioned simple interferometric measurement.

For this purpose, the second measurement light source 234 emits inter alia a measurement light bundle 234.1 which travels to the reference element 240 via a beam splitter 244. The incident measurement light bundle 234.1 passes through the partially reflective reference element 240 and, on the exit side, it is partially reflected on a surface region 240.1 of the optical reference surface so that a returning reference wave is formed. The transmitted fraction passes through the optical cavity 241 formed between the reference element 240 and the first measurement mirror 237, and is reflected on a first surface region 237.1 of the measurement mirror 237.

Unlike in the embodiment of FIG. 3, the surface normals of the reference surface 240.1 and of the first surface region 237.1 (in a setpoint state) are arranged mutually parallel so that the measurement light bundle 234.1 (in this setpoint state) is folded back on itself. From the first surface region 237.1, the measurement light bundle 234.1 is reflected inside the cavity 241 back to the reference body 240, and again strikes the partially reflective surface region 240.1 where it is reflected again and folded back on itself.

In this variant as well, multiple reflection of the measurement light bundle 234.1 thus also takes place in the cavity 241, and each time the measurement light bundle 234.1 is incident on the partially reflective surface region 240.1 a part of the measurement light bundle 234.1 emerges from the cavity 241 and is guided by the beam splitter 244 onto the capturing unit 236.

Using so-called white light interferometry, these multiple reflections can be selected. To this end, a so-called white light interferometer (more strictly speaking an interferometer with a spatially short-coherence light source) is combined with a retardation section, as is known from U.S. Pat. No. 5,361,312 (Küchel), the entire disclosure of which is incorporated herein by reference.

A spatially short-coherence light source 234.4 couples quasi-monochromatic light into a retardation section 234.5. Downstream of the retardation section 234.5, the light is launched into a single-mode light guide fibre 234.6 and guided to the cavity 241 with a collimator 234.7, as is known from WO 2006/102997 A1 (Altenberger et al.), the entire disclosure of which is incorporated herein by reference. The light guide fibre 234.6 eliminates aberrations or tilts of the wavefront downstream of the retardation section 234.5 and allows a flexible spatial arrangement of the components. The retardation D in the retardation section 234.5 is adjusted so that it corresponds to the optical path length of the part of the multiply reflected measurement light bundle which has experienced the desired number of M reflections in the cavity 241. Thus, with the distance L1 (as measured in the direction of the measurement light bundle 234.1) between the surface region 237.1 and the surface region 240.1, the following applies:

$$D = M \cdot L1. \tag{1}$$

Only multiple reflected rays therefore contribute to the interference, although all the others contribute to a background brightness in the interferogram of the capturing unit 236. A similar procedure is adopted with the other optical elements 108 to 112, rendering further discussion apparent to those skilled in the art.

At this point it should be noted that the imaging method described in connection with FIGS. 3 and 4 can also be carried out with this alternative embodiment.

Third Embodiment

Figure 6:
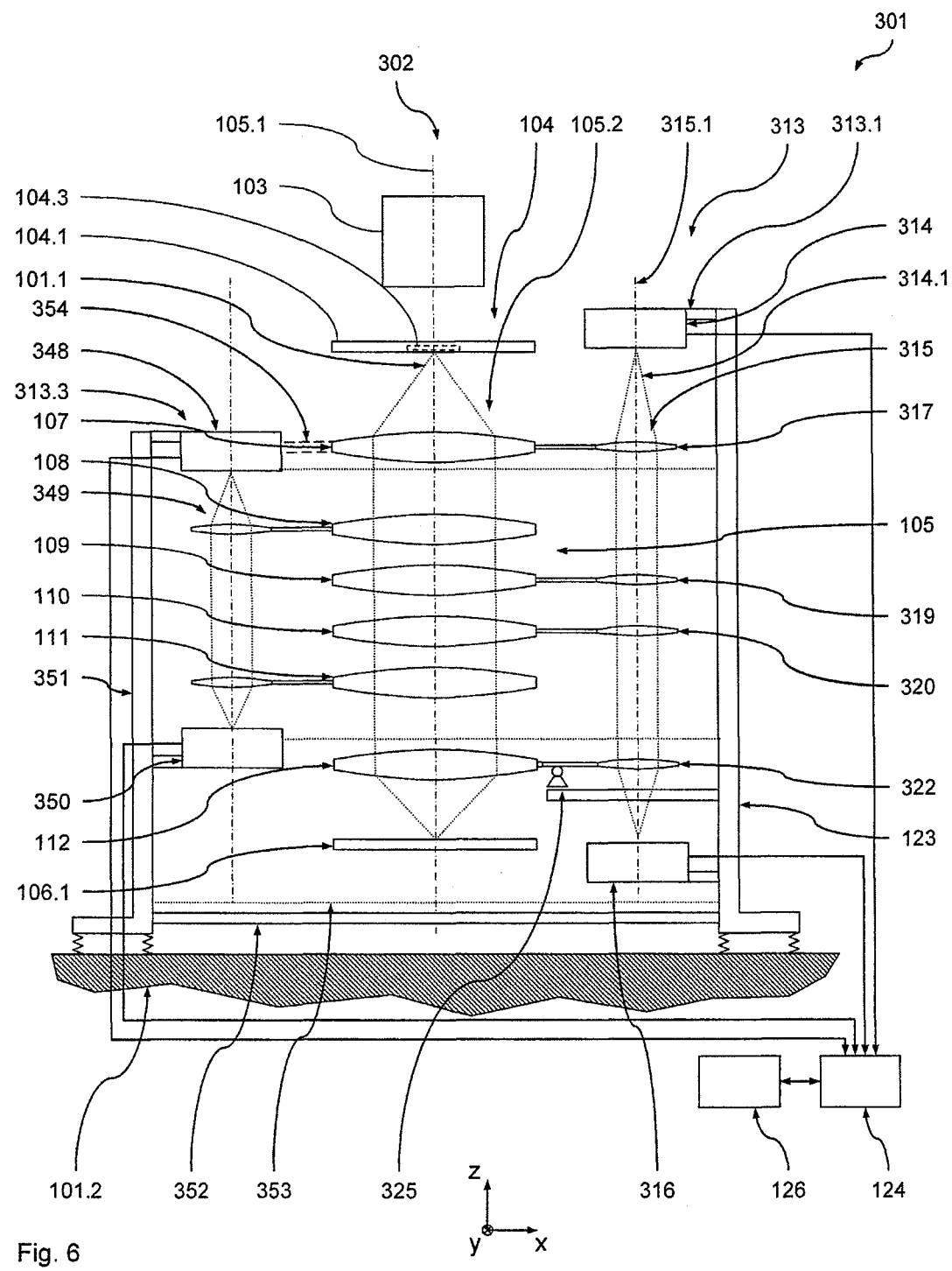
FIG. 6 is a highly schematised representation of another preferred embodiment of the optical imaging device according to the invention.

Another preferred embodiment of the microlithography device 301 according to the invention will be described below with reference to FIG. 6. FIG. 6 shows a schematic view of the microlithography device 301, which corresponds to the view of FIG. 1.

Basically, the microlithography device 201 corresponds in structure and functionality to the microlithography device 101 of FIGS. 1 to 3, so merely the differences will be discussed here. In particular, components of the same type are provided with references augmented by the value 200. Unless otherwise mentioned below, reference should be made to the comments above in connection with the first exemplary embodiment with respect of the properties of these components.

The material difference of the microlithography device 301 with respect to the embodiment of FIG. 1 consists in the configuration of the measuring device 313. More precisely, the capturing of the state changes of the first optical elements 107 to 112 is carried out with two measurement units 313.1 and 313.3.

The two measurement units 313.1 and 313.3 are arranged rotated with respect to the optical axis 105.1 of the objective 105 by 180°. The measurement unit 313.1 captures (in a similar way to the first measurement unit 113.1) the state changes of the first optical elements 107, 109, 110 and 112, while the measurement unit 313.3 (likewise in a similar way to the first measurement unit 113.1) captures the state changes of the first optical elements 108 and 111. To this end, the measurement unit 313.3 has a further measurement light source 348, a further optical element group 349 and a further capturing unit 350.

The measurement light source 348 and the capturing unit 350 are again rigidly fastened on a further reference structure 351 which is connected through a rigid connection 352 to the reference structure 123 so that there is a spatial relationship, defined at all times, between the reference structure 123 and the reference structure 351. Owing to this spatial relationship, defined at all times, between the reference structures 123 and 351 the processing unit 124 can deduce the current state changes of the first optical elements 107 to 112 from the signals of the capturing units 315 and 350 in the manner described above in connection with the first embodiment.

It is, however, to be understood that in other variants of the invention the spatial relationship between the reference structure 123 and the reference structure 351 may also be captured using a corresponding measuring device, as indicated in FIG. 6 by the dotted outline 353. With the aid of this information together with the capturing signals of the capturing units 315 and 350, the current state changes of the first optical elements 107 to 112 can likewise be deduced.

An interleaved arrangement of the two measurement units 313.1 and 313.3 is shown in the present example, in which first optical elements whose state change is acquired by one measurement unit are arranged spatially between first optical elements whose state change is acquired by the other measurement unit. It is, however, to be understood that, in other variants of the invention, the capturing of the state changes may be carried out by different measurement units which are not interleaved. For example, the state changes of the first optical elements 107 to 109 could be captured by one measurement unit and the state changes of the first optical elements 110 to 112 could be captured by another measurement unit. Naturally, more than two different measurement units could be provided for this.

It is furthermore to be understood that in other variants of the invention the measurement light source and/or the capturing unit of one of the measurement units may be connected not to a reference structure but to one of the first optical elements, the state change of which is captured by another measurement unit. Naturally, in this case the connection may preferably be configured so that, at all times, there is an accurately defined spatial relationship between the relevant components and the first optical element. In FIG. 6, this is indicated by the dashed outline 354.

At this point, it should be noted that the imaging method described in connection with FIGS. 3 and 4 may also be carried out with this alternative embodiment.

Fourth Embodiment

Figure 7:
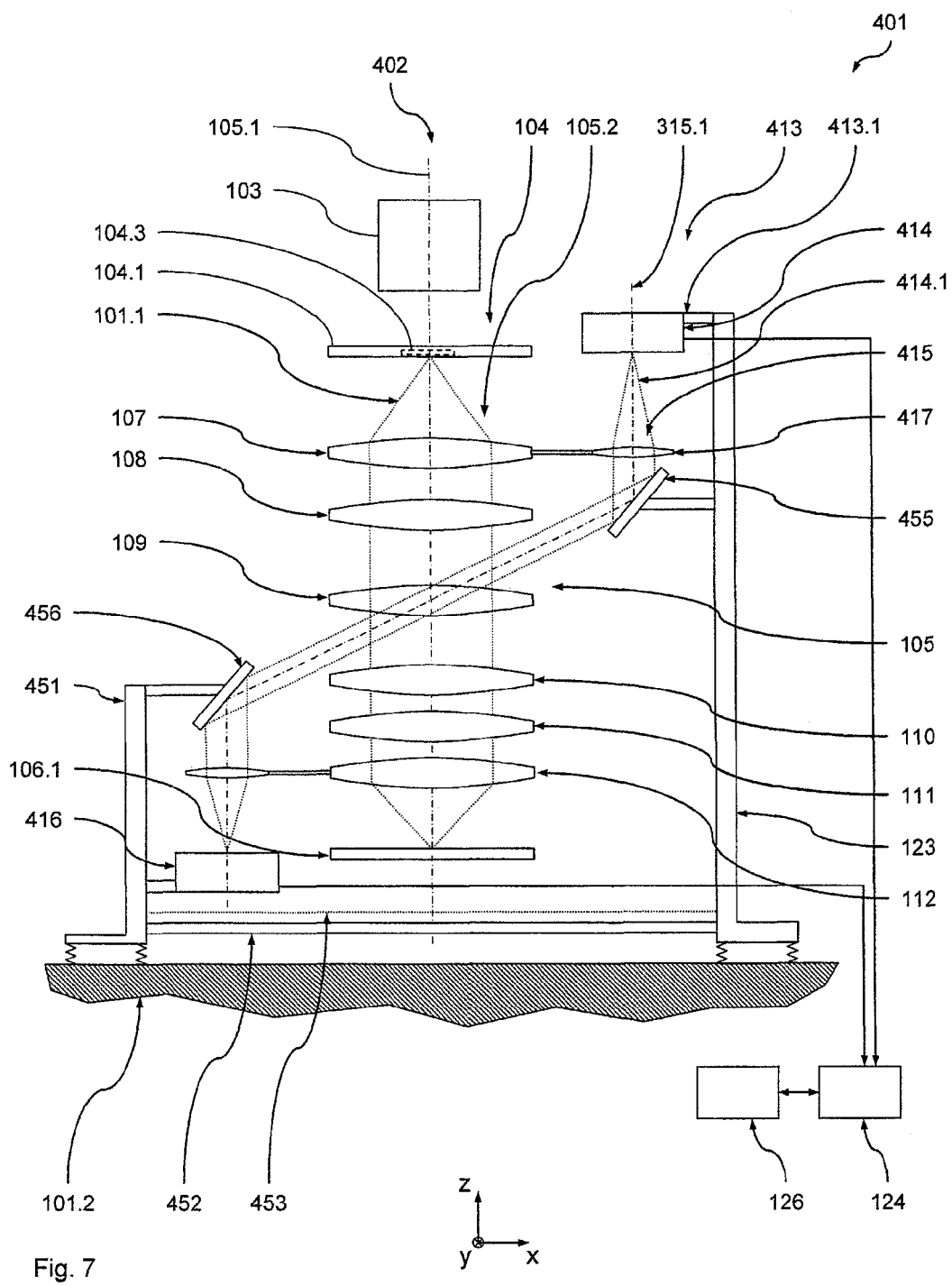
FIG. 7 is a highly schematised representation of another preferred embodiment of the optical imaging device according to the invention.

Another preferred embodiment of the microlithography device 401 according to the invention will be described below with reference to FIG. 7. FIG. 7 shows a schematic view of the microlithography device 401, which corresponds to the view of FIG. 1.

Basically, the microlithography device 401 corresponds in structure and functionality to the microlithography device 101 of FIG. 1, so merely the differences will be discussed here. In particular, components of the same type are provided with references augmented by the value 300. Unless otherwise mentioned below, reference should be made to the comments above in connection with the first embodiment with respect to the properties of these components.

The material difference of the microlithography device 401 with respect to the embodiment of FIG. 1 consists in the configuration of the measuring device 413. More precisely, the capturing of the state changes of the first optical elements 107 to 112 is carried out with a measurement unit 413.1, one of the second optical elements of the second optical element group 415 being formed by one of the first optical elements, namely the first optical element 109. To this end, the second optical element group 415 comprises guiding devices 455 and 456, which guide the measurement light bundle 414.1 such that it passes through the first optical element 109.

In this variant the measurement light source 414 is furthermore fastened on a reference structure 123, while the associated capturing unit 416 is arranged on a further reference structure 451. The measurement light source 414 and the capturing unit 416 are respectively fastened rigidly on the relevant reference structure 123 and 451, respectively, which are connected to one another through a rigid connection 452 so that there is a spatial relationship, defined accurately at all times, between the reference structure 123 and the reference structure 451. Owing to this spatial relationship, defined accurately at all times, between the reference structures 123 and 451, the processing unit 124 can deduce the current state changes of the first optical elements 107 to 112 from the signals of the capturing unit 416 in the manner described above in connection with the first embodiment.

It is, however, to be understood that, in other variants of the invention, the spatial relationship between the reference structure 123 and the reference structure 451 may also be captured using a corresponding measuring device, as indicated in FIG. 7 by the dotted outline 453. With the aid of this information, together with the capturing signals of the capturing unit 415, the current state changes of the first optical elements 107 to 112 can likewise be deduced.

They are arranged rotated with respect to the optical axis 105.1 of the objective 105 by 180°. The measurement unit 413.1 (in a similar way to the first measurement unit 113.1) captures the state changes of the first optical elements 107, 109, 110 and 112, while the measurement unit 413.3 (likewise in a similar way to the first measurement unit 113.1) captures the state changes of the first optical elements 108 and 111. To this end, the measurement unit 413.3 has a further measurement light source 448, a further optical element group 349 and a further capturing unit 450.

The measurement light source 348 and the capturing unit 350 are in turn fastened rigidly on a further reference structure 351, which is connected to the reference structure 123 through a rigid connection 352 so that there is a spatial relationship, defined accurately at all times, between the reference structure 123 and the reference structure 351. Owing to this spatial relationship, defined accurately at all times, between the reference structures 123 and 351, the processing unit 124 can deduce the current state changes of the first optical elements 107 to 112 from the signals of the capturing units 315 and 350 in the manner described above in connection with the first embodiment.

It is, however, to be understood that in other variants of the invention the spatial relationship between the reference structure 123 and the reference structure 351 may also be captured with a corresponding measuring device, as indicated in FIG. 6 by the dotted outline 353. With the aid of this information, together with the capturing signals of the capturing units 315 and 350, the current state changes of the first optical elements 107 to 112 can likewise be deduced.

In the present example, only one of the second optical elements of the second optical element group 415 is formed by one of the first optical elements 107 to 112. It is, however, to be understood that, in other variants of the invention, a different number of second optical elements of the second optical element group may also be formed by one of the first optical elements.

At this point, it should be noted that the imaging method described in connection with FIGS. 3 and 4 can also be carried out with this alternative embodiment.

The present invention may be used in connection with any production methods for electronic circuits. In this case, any desired working principles may be used, for example the so-called stepper principle. The invention is preferably used in connection with imaging devices operating according to the scanner principle, since the advantages of the present invention in respect of correcting the imaging errors of the imaging device are particularly effective in this case.

The present invention has been described above with the aid of examples, in which a multi-channel measurement (with a plurality of measurement light bundles) has only been described in connection with the first measurement unit 113.1. It is, however, to be understood that in other variants of the invention having a plurality of such measurement units, all or at least some of the other measurement units may also carry out such multichannel measurements (with a plurality of measurement light bundles). In other words, a multichannel functionality of the measurements carried out in the scope of the present invention can be achieved on the one hand by using a plurality of measurement units. Likewise, however, it is also possible for the respective measurement unit itself to carry out a multichannel measurement directly.

The present invention has been explained above with the aid of examples in which wavelengths in the EUV range are used for the exposure of the substrate. It should however be noted at this point that the invention may naturally also be used in connection with applications in which the exposure of a substrate, or another kind of imaging, is carried out with other wavelengths.

It should furthermore be noted that the present invention has been explained above with the aid of an example from the field of microlithography. It is, however, to be understood that the present invention may likewise be used for any other applications or imaging methods.

As noted, the description of the embodiments has been given by way of example. From the disclosure given, those skilled in the art will not only understand the present invention and its attendant advantages, but will also find apparent various changes and modifications to the structures and methods disclosed. The applicant seeks, therefore, to cover all such changes and modifications as fall within the spirit and scope of the invention, as defined by the appended claims, and equivalents thereof.

The invention claimed is:

1. Optical imaging device, comprising:
an imaging unit adapted to image an object point on an image point and
a measuring device, wherein:
the imaging unit comprises a first optical element group having at least one first optical element, which is adapted to contribute to the imaging of the object point on the image point,
the measuring device is adapted to determine at least one imaging error, which occurs when imaging the object point on the image point, using at least one capturing signal,
the measuring device comprises at least one measurement light source, a second optical element group and at least one capturing unit,
the measurement light source emits at least one measurement light bundle,
the second optical element group comprises at least one optical reference element and one second optical element, which are adapted to guide the at least one measurement light bundle onto the at least one capturing unit in order to generate the at least one capturing signal,
the second optical element has a defined spatial relationship with the first optical element,
the optical reference element has an at least partially reflective first optical surface and the second optical element has an at least partially reflective second optical surface, and wherein
the first optical surface and the second optical surface are arranged with respect to one another to produce multiple reflections of the at least one measurement light bundle between the first optical surface and the second optical surface,
the first optical surface has a plane first surface region and the second optical surface has a plane second surface region, the plane first surface region and the plane second surface region defining a path for at least some of the multiple reflections,
at least one of a first surface normal to the first surface region and a second surface normal to the second surface region are arranged inclined with respect to a beam axis of the at least one measurement light bundle,
the first optical surface or the second optical surface has a plane third surface region, and
a third surface normal to the third surface region is arranged inclined with respect to the first surface normal and the second surface normal so that the beam path of the at least one measurement light bundle folds back on itself after a predetermined number of reflections between the first surface region and the second surface region.

2. Optical imaging device according to claim 1, wherein the first optical surface and the second optical surface are arranged to form a Fizeau cavity.

3. Optical imaging device according to claim 1, wherein the first surface normal is arranged inclined with respect to the second surface normal.

4. Optical imaging device according to claim 1, wherein the beam path of the at least one measurement light bundle after a predetermined number of reflections between the first surface region and the second surface region folds back on itself.

5. Optical imaging device according to claim 1, wherein at least one of:
the reference element has an entry region at least partially transmissive for the at least one measurement light bundle, in which the at least one measurement light bundle enters a gap between the first optical surface and the second optical surface, and
the entry region has an optical entry surface at which a reference light bundle is reflected by partial reflection when the at least one measurement light bundle enters the gap between the first optical surface and the second optical surface.

6. Optical imaging device according to claim 1, wherein the second optical element has an entry region at least partially reflecting the at least one measurement light bundle, in which the at least one measurement light bundle strikes the first optical surface for the first time, and
the entry region has a diffractive element, at which a reference light bundle is generated by diffraction of the at least one measurement light bundle.

7. Optical imaging device according to claim 1, wherein the first optical surface and the second optical surface are arranged with respect to one another to produce at least five reflections of the at least one measurement light bundle between the first optical surface and the second optical surface.

8. Optical imaging device according to claim 1, wherein the second optical element group comprises a further second optical element,
the reference element and the further second optical element are adapted to guide at least one further measurement light bundle onto the at least one capturing unit to generate at least one further capturing signal,
the further second optical element has a defined spatial relationship with a further first optical element,
the further second optical element has an at least partially reflective third optical surface,
the measuring device is adapted to determine the at least one imaging error by using the at least one further capturing signal, the first optical surface and the third optical surface are assigned to one another to define a path for at least some of the multiple reflections of the at least one further measurement light bundle.

9. Optical imaging device according to claim 1, wherein at least one of:
the reference element is a component of a reference unit, which is adapted to impart a defined movement to the reference element,
a thermal shielding device is provided for at least one element of the second optical element group,
and
light with a first wavelength is provided for the imaging of the object point on the image point, and the at least one measurement light bundle comprises light with a second wavelength, the first wavelength differing from the second wavelength.

10. Optical imaging device according to claim 1, further comprising
a mask device adapted to receive a mask comprising a projection pattern, and a substrate device adapted to receive a substrate, and wherein
the first optical element group is adapted to image the projection pattern on the substrate,
the measuring device is adapted to determine an imaging error which occurs when imaging the projection pattern on the substrate as the at least one imaging error, and further comprising
a correction device adapted to correct the at least one imaging error,
the correction device comprising at least one control device connected to the measuring device and an actuator device connected to the control device, and wherein
the actuator device is adapted to actively influence at least one of: a position, an orientation, and a geometry of at least one of the first optical elements, the mask device, and the substrate device, and
the control device is adapted to drive the actuator device in accordance with the at least one imaging error determined by the measuring device.

11. Optical imaging device according to claim 1, further comprising
a mask device adapted to receive a mask comprising a projection pattern and a substrate device adapted to receive a substrate, and wherein
the first optical element group is adapted to image the projection pattern on the substrate,
the measuring device is adapted to determine an imaging error which occurs when imaging the projection pattern on the substrate as the at least one imaging error,
the measuring device is adapted to capture, at least in one degree of freedom, a spatial relationship of the measuring device to a reference on at least one of the mask device and the substrate device.

12. Optical imaging device according to claim 1, wherein
the measurement light source emits a plurality of measurement light bundles in a predetermined temporal relationship,
the second optical element group comprises a plurality of second optical elements, which are adapted to guide the measurement light bundles onto the at least one capturing unit in order to generate a plurality of capturing signals, and
the measuring device is adapted to determine the at least one imaging error by using the capturing signals of the at least one capturing unit.

13. Optical imaging device, comprising:
an imaging unit adapted to image an object point on an image point and
a measuring device, wherein:
the imaging unit comprises a first optical element group having at least one first optical element, which is adapted to contribute to the imaging of the object point on the image point,
the measuring device is adapted to determine at least one imaging error, which occurs when imaging the object point on the image point, using at least one capturing signal,
the measuring device comprises at least one measurement light source, a second optical element group and at least one capturing unit,
the measurement light source emits at least one measurement light bundle,
the second optical element group comprises at least one optical reference element and one second optical element, which are adapted to guide the at least one measurement light bundle onto the at least one capturing unit in order to generate the at least one capturing signal,
the second optical element has a defined spatial relationship with the first optical element,
the optical reference element has an at least partially reflective first optical surface and the second optical element has an at least partially reflective second optical surface, and wherein
the first optical surface and the second optical surface are arranged with respect to one another to produce multiple reflections of the at least one measurement light bundle between the first optical surface and the second optical surface,
the second optical element has an entry region at least partially reflecting the at least one measurement light bundle, in which the at least one measurement light bundle strikes the first optical surface for the first time, and
the entry region has a diffractive element, at which a reference light bundle is generated by diffraction of the at least one measurement light bundle.

14. Optical imaging device according to claim 13, wherein the diffractive element is a Littrow grating.

15. Optical imaging device according to claim 13, wherein the first optical surface and the second optical surface are arranged to form a Fizeau cavity.

16. Optical imaging device according to claim 13, wherein the first optical surface and the second optical surface are arranged with respect to one another to produce at least five reflections of the at least one measurement light bundle between the first optical surface and the second optical surface.

17. Optical imaging device according to claim 13, wherein
the second optical element group comprises a further second optical element,
the reference element and the further second optical element are adapted to guide at least one further measurement light bundle onto the at least one capturing unit in order to generate at least one further capturing signal,
the further second optical element has a defined spatial relationship with a further first optical element,
the further second optical element has an at least partially reflective third optical surface,
the measuring device is adapted to determine the at least one imaging error by using the at least one further capturing signal, the first optical surface and the third optical surface are assigned to one another to define a path for at least some of the multiple reflections of the at least one further measurement light bundle.

18. Optical imaging device according to claim 13, wherein at least one of
- the reference element is a component of a reference unit, which is adapted to impart a defined movement to the reference element,
- a thermal shielding device is provided for at least one element of the second optical element group, and
- light with a first wavelength is provided for the imaging of the object point on the image point, and the at least one measurement light bundle comprises light with a second wavelength, the first wavelength differing from the second wavelength.

19. Optical imaging device according to claim 13, further comprising
- a mask device adapted to receive a mask comprising a projection pattern and a substrate device adapted to receive a substrate, and wherein
- the first optical element group is adapted to image the projection pattern on the substrate,
- the measuring device is adapted to determine an imaging error which occurs when imaging the projection pattern on the substrate as the at least one imaging error, and further comprising
- a correction device adapted to correct the at least one imaging error,
- the correction device comprising at least one control device connected to the measuring device and an actuator device connected to the control device, and wherein
- the actuator device is adapted to actively influence at least one of a position, an orientation, and a geometry of at least one of the first optical elements, the mask device, and the substrate device, and
- the control device is adapted to drive the actuator device as a function of the at least one imaging error determined by the measuring device.

20. Optical imaging device according to claim 13, further comprising
- a mask device adapted to receive a mask comprising a projection pattern and a substrate device adapted to receive a substrate, and wherein
- the first optical element group is adapted to image the projection pattern on the substrate,
- the measuring device is adapted to determine an imaging error which occurs when imaging the projection pattern on the substrate as the at least one imaging error,
- the measuring device is adapted to capture, at least in one degree of freedom, a spatial relationship of the measuring device to a reference on at least one of the mask device and the substrate device.

21. Optical imaging device according to claim 13, wherein
- the measurement light source emits a plurality of measurement light bundles in a predetermined temporal relationship,
- the second optical element group comprises a plurality of second optical elements, which are adapted to guide the measurement light bundles onto the at least one capturing unit in order to generate a plurality of capturing signals, and
- the measuring device is adapted to determine the at least one imaging error by using the capturing signals of the at least one capturing unit.

22. Imaging method for microlithography, comprising imaging an object point on an image point using an optical imaging device according to claim 1.

23. Imaging method for microlithography, comprising imaging an object point on an image point using an optical imaging device according to claim 13.

* * * * *

UNITED STATES PATENT AND TRADEMARK OFFICE
CERTIFICATE OF CORRECTION

PATENT NO. : 8,537,333 B2
APPLICATION NO. : 12/983735
DATED : September 17, 2013
INVENTOR(S) : Rolf Freimann and Ulrich Wegmann It is certified that error appears in the above-identified patent and that said Letters Patent is hereby corrected as shown below:

In the Specification

Column 7, Line 24: delete "$0.6.10^{-6}K^{-1}$," and insert -- $0.6 \cdot 10^{-6}K^{-1}$, --

Signed and Sealed this
Sixth Day of May, 2014

Michelle K. Lee
*Deputy Director of the United States Patent and Trademark Office*